United States Patent [19]
Ausubel et al.

[11] Patent Number: 6,127,607
[45] Date of Patent: Oct. 3, 2000

[54] PLANT RESISTANCE GENE FAMILY ENCODING RESISTANCE POLYPEPTIDES HAVING P-LOOP AND LRR MOTIFS

[75] Inventors: Frederick Michael Ausubel, Newton, Mass.; Brian J. Staskawicz, Castro Valley, Calif.; Andrew F. Bent, Piedmont, Calif.; Douglas Dahlbeck, Castro Valley, Calif.; Fumiaki Katagiri, Somerville, Mass.; Barbara N. Kunkel, St. Louis, Mo.; Michael Nicholas Mindrinos, Somerville, Mass.; Guo-Liang Yu, Darnestown, Md.

[73] Assignees: The General Hospital Corporation, Boston, Mass.; The Regents of the University of California, Oakland, Calif.

[21] Appl. No.: 08/841,089

[22] Filed: Apr. 29, 1997

Related U.S. Application Data

[63] Continuation of application No. 08/227,360, Apr. 13, 1994, abandoned.

[51] Int. Cl.[7] .............................. A01H 5/00; A01H 5/10; C12N 1/21; C12N 5/14

[52] U.S. Cl. .................... 800/301; 435/69.1; 435/252.3; 435/320.1; 435/411; 435/412; 435/415; 435/419; 536/23.6; 800/279; 800/312; 800/313; 800/317.4; 800/320.1; 800/320.2; 800/320.3

[58] Field of Search ............................ 435/172.3, 320.1, 435/69.1, 419, 468, 252.3, 411, 412, 415; 536/23.6; 800/205, 250, 279, 301, 312, 313, 317.4, 320.4, 320.2, 320.3

[56] References Cited

U.S. PATENT DOCUMENTS

| | | | |
|---|---|---|---|
| 5,237,056 | 8/1993 | Fischbach | 536/23.5 |
| 5,571,706 | 11/1996 | Baker et al. | 800/279 |
| 5,866,776 | 2/1999 | Marie de Wit | 800/279 |

FOREIGN PATENT DOCUMENTS

| | | |
|---|---|---|
| 0 544 250 A2 | 6/1993 | European Pat. Off. |
| 0 686 696 A1 | 12/1995 | European Pat. Off. |
| 0 874 055 A2 | 10/1998 | European Pat. Off. |
| 90/12097 | 10/1990 | WIPO |
| 91/15585 | 10/1991 | WIPO |
| WO 91/15585 | 10/1991 | WIPO |
| 93/11241 | 6/1993 | WIPO |
| 95/18230 | 7/1995 | WIPO |
| 95/28423 | 10/1995 | WIPO |
| 95/29238 | 11/1995 | WIPO |
| 95/31560 | 11/1995 | WIPO |
| 95/31564 | 11/1995 | WIPO |
| 95/35024 | 12/1995 | WIPO |

OTHER PUBLICATIONS

Ausubel et al., "Use of *Arabidopsis thaliana* defense–related mutants to dissect the plant response to pathogens," *Proc. Natl. Acad. Sci. USA,* 92:4189–4196 (1995) "Self–Defense by Plants: Induction and Signalling Pathways," Paper presented at Colloquium held by National Academy of Sciences in Irvine, CA.

Baker et al., "Isolation of the Tobacco Mosaic Virus Resistance Gene N," *Advances in Molecular Genetics of Plant–Microbe Interactions,* 3:297–302, (1994).

Carmona et al., "Expression of the alpha–thionin gene from barley in tobacco confers enhanced resistance to bacterial pathogens," *The Plant Journal,* 3:457–482 (1993).

Chasan, "Meeting Report: Plant–Pathogen Encounters in Edinburgh," *The Plant Cell,* 10:1332–1341 (1994).

Cornelissen et al.,"Strategies for Control of Fungal Diseases with Transgenic Plants," *The Plant Physiology,* 101:709–712 (1993).

Dinesh–Kumar et al., "Transposon tagging of tobacco mosaic virus resistance gene N/: Its possible role in the TMV–N–mediated signal transduction pathway," *Proc. Natl. Acad. Sci. USA,* 92:4175–4180 (1995).

Ellis et al., "Contrasting complexity of the two rust resistance loci in flax," *Proc. Nat. Acad. Sci. USA,* 92:4185–4188, (1995).

Gould et al., "Use of the DNA polymerase chain reaction for homology probing: Isolation of partial cDNA or genomic clones encoding the iron–sulfur protein of succinate dehydrogenase from several species," *Proc. Natl. Acad. Sci. USA,* 86:1934–1935 (1989).

Keen,"The molecular biology of disease resistance," *Plant Molecular Biology,* 19:109–122 (1992).

Lamb et al.,"Emerging Strategies for Enhancing Crop Resistance in Microbial Pathogens," *Bio/Technology,* 10:1436–1445 (1992).

Mahon et al., "The small cardioactive peptides A and B of Apkysia are derived from a common precursor molecule," *Proc. Natl. Acad. Sci, USA,* 82:3925–3929 (1985).

Phillips and Gigot, "The *Arabidopsis thaliana* transcribed genome: the GDR cDNA progarm" unpublished (1995).

Staskawicz et al., "Genetic analysis of bacterial disease resistance in Arabidopsis and closing of the RPS2 resistance gene," *Curr. Plant Sci, Biotechnol. Agric,* 21:283–288 (1994).

Staskawicz et al., "Genetic Dissection of Bacterial Disease Resistance," *Chemical Abstracts,* 123(11) (1995).

Stotz et al., "Molecular Characterization of a Polygalacturonase Inhibitor from *Pyrys communis* L. cv Bartlett," *Plant Physiol.,* 102:133–138 (1993).

Whitham et al., "*Nicotiana glutinosa* virus resistance (N) gene, complete cds," EMBL Sequence Accession No. U15605, (1994).

(List continued on next page.)

*Primary Examiner*—Amy J. Nelson
*Attorney, Agent, or Firm*—Karen L. Elbing; James D. DeCamp; Clark & Elbing LLP

[57] ABSTRACT

Disclosed is a new plant resistance gene family, the members of which encode plant resistance polypeptides having P-loop and LRR structural motifs. Also disclosed are substantially pure plant DNAs encoding such polypeptides. The invention further involves transgenic plants and transformed host cells that express these DNAs and exhibit enhanced disease resistance to plant pathogens.

113 Claims, 12 Drawing Sheets

OTHER PUBLICATIONS

Kunkel et al.; RPS2, an Arabidopsis Disease Resistance Locus Specifying Recognition of *Pseudomonas syringae* Strains Expressing the Avirulence Gene avrRpt2; The Plant Cell, vol. 5, 865–875, Aug. 1993; Berkeley, CA.

Joosten et al.; Host resistance to a fungal tomato pathogen lost by a single base–pair change in an avirulence gene; Nature, vol. 367 p. 384–386; Jan. 27, 1994; The Netherlands.

Dong et al.; Induction of Arabidopsis Defense Genes by Virulent and Avirulent *Pseudomonas syringae* Strains and by a Cloned Avirulence Gene; The Plant Cell, vol. 3, 61–72, Jan. 1991; Columbus, Ohio.

Innes et al.; Molecular Analysis of Avirulence Gene avrRpt2 and Identification of a Putative Regulatory Sequence Common to All Known *Pseudomonas syringae* Avirulence Genes; J. Bacteriology vol. 175, No. 15. Aug. 1993, pp. 4859–4869; Berkeley, CA.

Johal et al.; Reductase Activity Encoded by the HM1 Disease Resistance Gene in Maize; Science, vol. 258, Nov. 6, 1992; Johnston, IA.

Martin et al.; Map–Based Cloning of a Protein Kinase Gene Conferring Disease Resistance in Tomato; Science vol. 262, Nov. 26, 1993; pp. 1432–1436.

Whalen et al.; Identification of *Pseudomonas syringae* Pathogens of Arabidopsis and a Bacterial Locus Determining Avirulence on Both Arabidopsis and Soybean; The Plant Cell. vol. 3, 49–59; Jan. 1991.

Guo–Liang Yu et al.; Arabidopsis Mutations at the RPS2 Locus Result in Loss of Resistance to *Pseudomonas syringae* Strains Expressing the Avirulence Gene avrRpt2; MPMI vol. 6, No. 4 pp. 434–443; Boston, MA, 1993.

Wanner et al.; Recognition of the Avirulence Gene avrB from *Pseudomonas syringae* pv. *glycinea* by *Arabidopsis thaliana*; MPMI, vol. 6, No. 5, 1993, pp. 582–591; Columbus.

Lister et al.; Recombinant inbred lines for mapping RFLP and phenotypic markers in *Arabidopsis thaliana*; The Plant Journal vol. 4 (4), pp. 745–750 1993; United Kingdom.

Hahn et al.; Cultivar–Specific Elicitation of Barley Defense Reactions by the Phytotoxic Peptide NIP1 from *Rhynchosporium secalis*; MPMI vol. 6, pp. 745–754 1993.

Gabriel et al.; Gene–for–gene interactions of five cloned avirulence genes from *Xanthomonas campestris* pv. *malvacearum* with specific resistance genes in cotton; Proc. Natl. Acad. Sci USA vol. 83, pp. 6415–6419; 1986.

Staskawicz et al.; Molecular Characterization of Cloned Avirulence Genes from Race 0 and Race 1 of *Pseudomonas syringae* pv. *glycinea*; Jour. of Bacterioloby, pp. 5789–5794, Dec. 1987.

Van den Ackerveken et al.; Molecular analysis of the avirulence gene avr9 of the fungal tomato pathogen *Cladosporium fulvum* fully supports the gene–for–gene hypothesis; The Plant Jour. vol. 2(3) pp. 359–366; 1992.

Kobayashi et al.; Molecular Characterization of Avirulence Gene D from *Pseudomonas syringae* pv. tomato; Molecular Plant–Microbe Interactions, vol. 3, No. 2, pp. 94–102, 1990.

Kobayashi et al.; A Gene from *Pseudomonas syringae* pv. *glycinea* with Homology to Avirulence Gene D from P.s pv. tomatio but Devoid of the Avirulence Phenotype; MPM1 vol. 3, No. 2 pp. 103–111, 1990.

Arlat et al.; PopA1, a protein which induces a hypersensitivity–like response on specific Petunia genotypes, is secreted via the Hrp pathway of *Pseudomonas solanacearum*; The EMBO Jour. vol. 13 No. 3 pp. 543–553; 1994.

Keen et al.; Host Range Determinants in Plant Pathogens and Symbionts; Ann. Rev. Microbiol. 42:421–40 1988.

Ellingboe; Changing Concepts in Host–Pathogen Genetics; Ann. Rev. Phytopathol. 19:125–43 1981.

Gabriel et al.; Working Models of Specific Recognition in Plant–Microbe Interactions; Annu. Reb Phytopathol 28:365–91, 1990.

Flor; Current Status of the Gene–for–Gene Concept; Ann. Rev. Phytopathol. 9:275–296 (1971).

Midland et al.; The Structures of Syringolides 1 and 2, Novel C–Glycosidic Elicitors from *Pseudomonas syringae* pv. tomato; J. Org. Chem. vol. 58, pp. 2940–2945 1993.

Keen et al.; Plant Disease Resistance Genes: Interactions with Pathogens and Their Improved Utilization to Control Plant Diseases; Biotochnology in Plant Disease Control, pp. 65–88, 1993.

Bent et al., Science 265:1856–1860 (1994).

Bunz et al., Proc. Natl. Acad. Sci. USA 90:11014–11018 (1993).

Burbelo et al., Proc. Natl. Acad. Sci. USA 90:11543–11547 (1993).

Lu et al., Biochemical and Biophysical Research Communications 193(2):779–786 (1993).

Mindrinos et al., Cell 78:1089–1099 (1994).

Whitman et al., Cell 78:1101–1115 (1994).

Phillips et al., "A *Thaliana* Transcribed Sequence; Clone TASG104, 5' end, " EMBL Sequence Accession No. Z17993, Nov. 6, 1992, XP002063426.

Staskawicz et al., "Genetic Dissection of Bacterial Disease Resistance," J. Cellular Biochemistry Supplement vol. 18a, Jan. 1994, p. 75 XP002063232.

Rothstein SJ, et al. "Promoter cassettes, antibiotic–resistance genes, and vectors for plant transformation." Gene 53: 153–161, 1987.

Whalen et al (1991) The Plant Cell 3:49–59.

Kobayashi, et al (1990) Molecular Plant–Microbe Interactions 3(2):94–102, 103–111.

Kunkel et al (Aug. 1993) The Plant Cell 5:865–875.

Dean (1993) Phil. Trans. R. Soc. Lond. B 342:189–195.

Dalrymple, et al (1993) Molecular and Biochemical Parasitology 59:181–190.

Newman, et al (1994) Plant Physiology 106:1241–1255.

Boswell, et al. in *Computational Molecular Biology* sources and methods for sequence analysis (Lesk, ed.) Oxford University Press, Oxford, 1988, pp. 170–171.

Lawrence, et al (Aug. 1995) The Plant Cell 7:1195–1206.

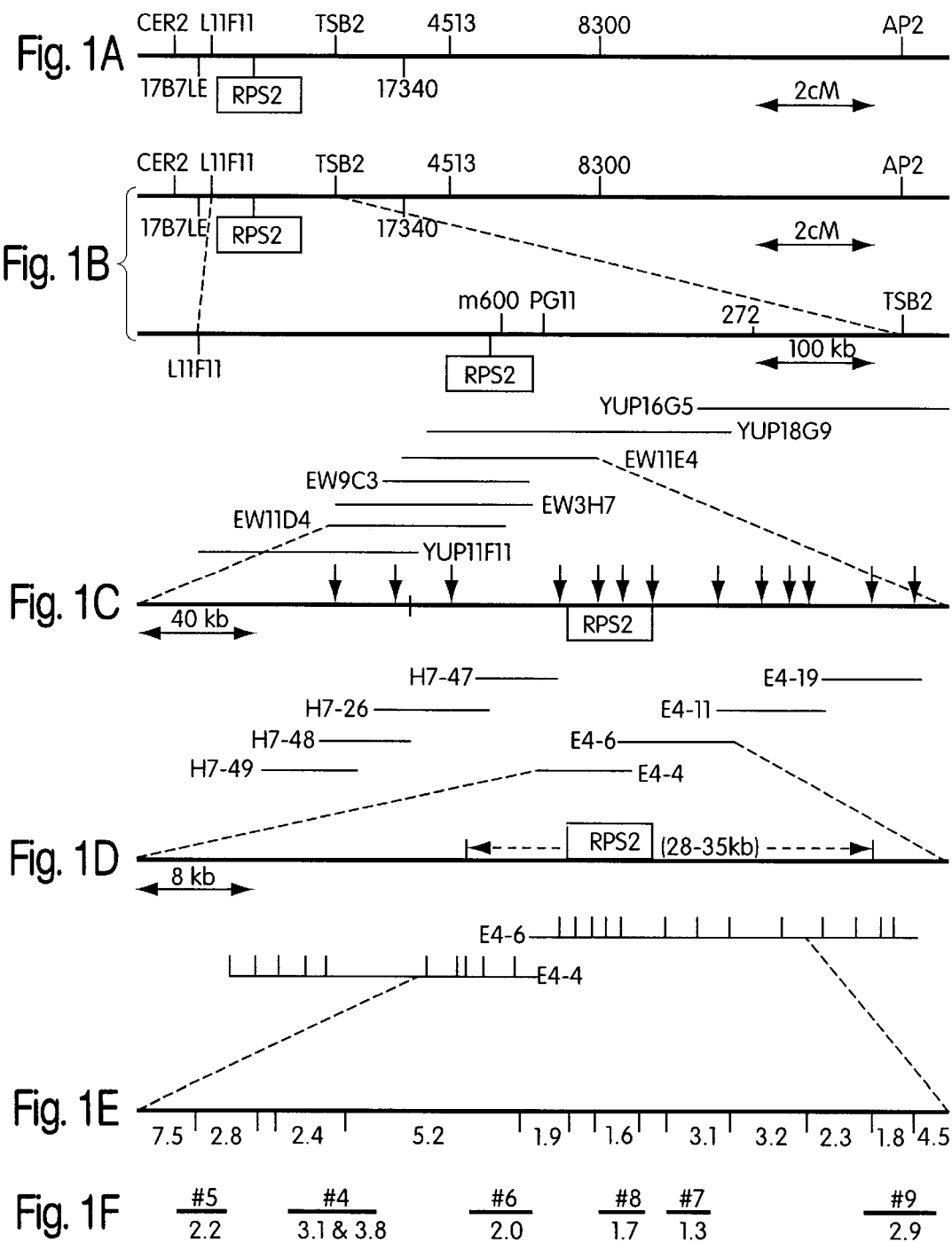

```
      AAGTAAAAGAAAGAGCGAGAAATCATCGAAATGGATTTCATCTCATCTCTTATCGTTGGC
  1   ---------+---------+---------+---------+---------+---------+  60
      TTCATTTTCTTTCTCGCTCTTTAGTAGCTTTACCTAAAGTAGAGTAGAGAATAGCAACCG a     K * K K E R E I I E Ⓜ D F I S S L I V G     -
b       S K R K S E K S S K W I S S H L L S L A   -
c         V K E R A R N H R N G F H L I S Y R W L -

TGTGCTCAGGTGTTGTGTGAATCTATGAATATGGCGGAGAGAAGAGGACATAAGACTGAT
 61   ---------+---------+---------+---------+---------+---------+ 120
      ACACGAGTCCACAACACACTTAGATACTTATACCGCCTCTCTTCTCCTGTATTCTGACTA a     C A Q V L C E S M N M A E R R G H K T D     -
b       V L R C C V N L * I W R R E E D I R L I   -
c         C S G V V * I Y E Y G G E K R T * D * S -

CTTAGACAAGCCATCACTGATCTTGAAACAGCCATCGGTGACTTGAAGGCCATACGTGAT
121   ---------+---------+---------+---------+---------+---------+ 180
      GAATCTGTTCGGTAGTGACTAGAACTTTGTCGGTAGCCACTGAACTTCCGGTATGCACTA a     L R Q A I T D L E T A I G D L K A I R D     -
b       L D K P S L I L K Q P S V T * R P Y V M   -
c         * T S H H * S * N S H R * L E G H T * * -

GACCTGACTTTACGGATCCAACAAGACGGTCTAGAGGGACGAAGCTGCTCAAATCGTGCC
181   ---------+---------+---------+---------+---------+---------+ 240
      CTGGACTGAAATGCCTAGGTTGTTCTGCCAGATCTCCCTGCTTCGACGAGTTTAGCACGG a     D L T L R I Q Q D G L E G R S C S N R A     -
b       T * L Y G S N K T V * R D E A A Q I V P   -
c         P D F T D P T R R S R G T K L L K S C Q -

AGAGAGTGGCTTAGTGCGGTGCAAGTAACGGAGACTAAAACAGCCCTACTTTTAGTGAGG
241   ---------+---------+---------+---------+---------+---------+ 300
      TCTCTCACCGAATCACGCCACGTTCATTGCCTCTGATTTTGTCGGGATGAAAATCACTCC a     R E W L S A V Q V T E T K T A L L L V R     -
b       E S G L V R C K * R R L K Q P Y F * * G   -
c         R V A * C G A S N G D * N S P T F S E V -

TTTAGGCGTCGGGAACAGAGGACGCGAATGAGGAGGAGATACCTCAGTTGTTTCGGTTGT
301   ---------+---------+---------+---------+---------+---------+ 360
      AAATCCGCAGCCCTTGTCTCCTGCGCTTACTCCTCCTCTATGGAGTCAACAAAGCCAACA a     F R R R E Q R T R M R R R Y L S C F G C     -
b       L G V G N R G R E * G G D T S V V S V V   -
c         * A S G T E D A N E E E I P Q L F R L C -

GCCGACTACAAACTGTGCAAGAAGGTTTCTGCCATATTGAAGAGCATTGGTGAGCTGAGA
361   ---------+---------+---------+---------+---------+---------+ 420
      CGGCTGATGTTTGACACGTTCTTCCAAAGACGGTATAACTTCTCGTAACCACTCGACTCT
```

GAACGCTCTGAAGCTATCAAAACAGATGGCGGGTCAATTCAAGTAACTTGTAGAGAGATA
421   ---------+---------+---------+---------+---------+---------+ 480
      CTTGCGAGACTTCGATAGTTTTGTCTACCGCCCAGTTAAGTTCATTGAACATCTCTCTAT a   E R S E A I K T D G G S I Q V T C R E I   -
b     N A L K L S K Q M A G Q F K * L V E R Y -
c       T L * S Y Q N R W R V N S S N L * R D T -

CCCATCAAGTCCGTTGTCGGAAATACCACGATGATGGAACAGGTTTTGGAATTTCTCAGT
481   ---------+---------+---------+---------+---------+---------+ 540
      GGGTAGTTCAGGCAACAGCCTTTATGGTGCTACTACCTTGTCCAAAACCTTAAAGAGTCA a   P I K S V V G N T T M M E Q V L E F L S   -
b     P S S P L S E I P R * W N R F W N F S V -
c       H Q V R C R K Y H D D G T G F G I S Q * -

GAAGAAGAAGAAAGAGGAATCATTGGTGTTTATGGACCTGGTGGGGTTGGGAAGACAACG
541   ---------+---------+---------+---------+---------+---------+ 600
      CTTCTTCTTCTTTCTCCTTAGTAACCACAAATACCTGGACCACCCCAACCCTTCTGTTGC a   E E E E R G I I G V Y G P G G V G K T T   -
b     K K K K E E S L V F M D L V G L G R Q R -
c       R R R K R N H W C L W T W W G W E D N V -

TTAATGCAGAGCATTAACAACGAGCTGATCACAAAAGGACATCAGTATGATGTACTGATT
601   ---------+---------+---------+---------+---------+---------+ 660
      AATTACGTCTCGTAATTGTTGCTCGACTAGTGTTTTCCTGTAGTCATACTACATGACTAA a   L M Q S I N N E L I T K G H Q Y D V L I   -
b     * C R A L T T S * S Q K D I S M M Y * F -
c       N A E H * Q R A D H K R T S V * C T D L -

TGGGTTCAAATGTCCAGAGAATTCGGCGAGTGTACAATTCAGCAAGCCGTTGGAGCACGG
661   ---------+---------+---------+---------+---------+---------+ 720
      ACCCAAGTTTACAGGTCTCTTAAGCCGCTCACATGTTAAGTCGTTCGGCAACCTCGTGCC a   W V Q M S R E F G E C T I Q Q A V G A R   -
b     G F K C P E N S A S V Q F S K P L E H G -
c       G S N V Q R I R R V Y N S A S R W S T V -

TTGGGTTTATCTTGGGACGAGAAGGAGACCGGCGAAAACAGAGCTTTGAAGATATACAGA
721   ---------+---------+---------+---------+---------+---------+ 780
      AACCCAAATAGAACCCTGCTCTTCCTCTGGCCGCTTTTGTCTCGAAACTTCTATATGTCT a   L G L S W D E K E T G E N R A L K I Y R   -
b     W V Y L G T R R R P A K T E L * R Y T E -
c       G F I L G R E G D R R K Q S F E D I Q S -

GCTTTGAGACAGAAACGTTTCTTGTTGTTGCTAGATGATGTCTGGGAAGAGATAGACTTG
781   ---------+---------+---------+---------+---------+---------+ 840
      CGAAACTCTGTCTTTGCAAAGAACAACAACGATCTACTACAGACCCTTCTCTATCTGAAC
```

GAGAAAACTGGAGTTCCTCGACCTGACAGGGAAAACAAATGCAAGGTGATGTTCACGACA
841   ---------+---------+---------+---------+---------+---------+ 900
      CTCTTTTGACCTCAAGGAGCTGGACTGTCCCTTTTGTTTACGTTCCACTACAAGTGCTGT a   E  K  T  G  V  P  R  P  D  R  E  N  K  C  K  V  M  F  T  T   -
b     R  K  L  E  F  L  D  L  T  G  K  T  N  A  R  *  C  S  R  H -
c        E  N  W  S  S  S  T  *  Q  G  K  Q  M  Q  G  D  V  H  D  T-

CGGTCTATAGCATTATGCAACAATATGGGTGCGGAATACAAGTTGAGAGTGGAGTTTCTG
901   ---------+---------+---------+---------+---------+---------+ 960
      GCCAGATATCGTAATACGTTGTTATACCCACGCCTTATGTTCAACTCTCACCTCAAAGAC a   R  S  I  A  L  C  N  N  M  G  A  E  Y  K  L  R  V  E  F  L   -
b     G  L  *  H  Y  A  T  I  W  V  R  N  T  S  *  E  W  S  F  W -
c        V  Y  S  I  M  Q  Q  Y  G  C  G  I  Q  V  E  S  G  V  S  G-

GAGAAGAAACACGCGTGGGAGCTGTTCTGTAGTAAGGTATGGAGAAAAGATCTTTTAGAG
961   ---------+---------+---------+---------+---------+---------+ 1020
      CTCTTCTTTGTGCGCACCCTCGACAAGACATCATTCCATACCTCTTTTCTAGAAAATCTC a   E  K  K  H  A  W  E  L  F  C  S  K  V  W  R  K  D  L  L  E   -
b     R  R  N  T  R  G  S  C  S  V  V  R  Y  G  E  K  I  F  *  S -
c        E  E  T  R  V  G  A  V  L  *  *  G  M  E  K  R  S  F  R  V-

TCATCATCAATTCGCCGGCTCGCGGAGATTATAGTGAGTAAATGTGGAGGATTGCCACTA
1021  ---------+---------+---------+---------+---------+---------+ 1080
      AGTAGTAGTTAAGCGGCCGAGCGCCTCTAATATCACTCATTTACACCTCCTAACGGTGAT a   S  S  S  I  R  R  L  A  E  I  I  V  S  K  C  G  G  L  P  L   -
b     H  H  Q  F  A  G  S  R  R  L  *  *  V  N  V  E  D  C  H  * -
c        I  I  N  S  P  A  R  G  D  Y  S  E  *  M  W  R  I  A  T  S-

GCGTTGATCACTTTAGGAGGAGCCATGGCTCATAGAGAGACAGAAGAAGAGTGGATCCAT
1081  ---------+---------+---------+---------+---------+---------+ 1140
      CGCAACTAGTGAAATCCTCCTCGGTACCGAGTATCTCTCTGTCTTCTTCTCACCTAGGTA a   A  L  I  T  L  G  G  A  M  A  H  R  E  T  E  E  E  W  I  H   -
b     R  *  S  L  *  E  E  P  W  L  I  E  R  Q  K  K  S  G  S  M -
c        V  D  H  F  R  R  S  H  G  S  *  R  D  R  R  R  V  D  P  C-

GCTAGTGAAGTTCTGACTAGATTTCCAGCAGAGATGAAGGGTATGAACTATGTATTTGCC
1141  ---------+---------+---------+---------+---------+---------+ 1200
      CGATCACTTCAAGACTGATCTAAAGGTCGTCTCTACTTCCCATACTTGATACATAAACGG a   A  S  E  V  L  T  R  F  P  A  E  M  K  G  M  N  Y  V  F  A   -
b     L  V  K  F  *  L  D  F  Q  Q  R  *  R  V  *  T  M  Y  L  P -
c        *  *  S  S  D  *  I  S  S  R  D  E  G  Y  E  L  C  I  C  P-

CTTTTGAAATTCAGCTACGACAACCTCGAGAGTGATCTGCTTCGGTCTTGTTTCTTGTAC
1201  ---------+---------+---------+---------+---------+---------+ 1260
      GAAAACTTTAAGTCGATGCTGTTGGAGCTCTCACTAGACGAAGCCAGAACAAAGAACATG
```

TGCGCTTTATTCCCAGAAGAACATTCTATAGAGATCGAGCAGCTTGTTGAGTACTGGGTC
1261    ---------+---------+---------+---------+---------+---------+ 1320
        ACGCGAAATAAGGGTCTTCTTGTAAGATATCTCTAGCTCGTCGAACAACTCATGACCCAG a    C A L F P E E H S I E I E Q L V E Y W V    -
b      A L Y S Q K N I L * R S S S L L S T G S  -
c        R F I P R R T F Y R D R A A C * V L G R -

GGCGAAGGGTTTCTCACCAGCTCCCATGGCGTTAACACCATTTACAAGGGATATTTTCTC
1321    ---------+---------+---------+---------+---------+---------+ 1380
        CCGCTTCCCAAAGAGTGGTCGAGGGTACCGCAATTGTGGTAAATGTTCCCTATAAAAGAG a    G E G F L T S S H G V N T I Y K G Y F L    -
b      A K G F S P A P M A L T P F T R D I F S  -
c        R R V S H Q L P W R * H H L Q G I F S H -

ATTGGGGATCTGAAAGCGGCATGTTTGTTGGAAACCGGAGATGAGAAAACACAGGTGAAG
1381    ---------+---------+---------+---------+---------+---------+ 1440
        TAACCCCTAGACTTTCGCCGTACAAACAACCTTTGGCCTCTACTCTTTTGTGTCCACTTC a    I G D L K A A C L L E T G D E K T Q V K    -
b      L G I * K R H V C W K P E M R K H R * R  -
c        W G S E S G M F V G N R R * E N T G E D -

ATGCATAATGTGGTCAGAAGCTTTGCATTGTGGATGGCATCTGAACAGGGGACTTATAAG
1441    ---------+---------+---------+---------+---------+---------+ 1500
        TACGTATTACACCAGTCTTCGAAACGTAACACCTACCGTAGACTTGTCCCCTGAATATTC a    M H N V V R S F A L W M A S E Q G T Y K    -
b      C I M W S E A L H C G W H L N R G L I R  -
c        A * C G Q K L C I V D G I * T G D L * G -

GAGCTGATCCTAGTTGAGCCTAGCATGGGACATACTGAAGCTCCTAAAGCAGAAAACTGG
1501    ---------+---------+---------+---------+---------+---------+ 1560
        CTCGACTAGGATCAACTCGGATCGTACCCTGTATGACTTCGAGGATTTCGTCTTTTGACC a    E L I L V E P S M G H T E A P K A E N W    -
b      S * S * L S L A W D I L K L L K Q K T G  -
c        A D P S * A * H G T Y * S S * S R K L A -

CGACAAGCGTTGGTGATCTCATTGTTAGATAACAGAATCCAGACCTTGCCTGAAAAACTC
1561    ---------+---------+---------+---------+---------+---------+ 1620
        GCTGTTCGCAACCACTAGAGTAACAATCTATTGTCTTAGGTCTGGAACGGACTTTTTGAG a    R Q A L V I S L L D N R I Q T L P E K L    -
b      D K R W * S H C * I T E S R P C L K N S  -
c        T S V G D L I V R * Q N P D L A * K T H -
```

Fig. 2D

```
      ATATGCCCGAAACTGACAACACTGATGCTCCAACAGAACAGCTCTTTGAAGAAGATTCCA
1621  ------------------------------------------------------------  1680
      TATACGGGCTTTGACTGTTGTGACTACGAGGTTGTCTTGTCGAGAAACTTCTTCTAAGGT a      I  C  P  K  L  T  T  L  M  L  Q  Q  N  S  S  L  K  K  I  P  -
b       Y  A  R  N  *  Q  H  *  C  S  N  R  T  A  L  *  R  R  F  Q  -
c        M  P  E  T  D  N  T  D  A  P  T  E  Q  L  F  E  E  D  S  N -

ACAGGGTTTTTCATGCATATGCCTGTTCTCAGAGTCTTGGACTTGTCGTTCACAAGTATC
1681  ------------------------------------------------------------  1740
      TGTCCCAAAAAGTACGTATACGGACAAGAGTCTCAGAACCTGAACAGCAAGTGTTCATAG a      T  G  F  F  M  H  M  P  V  L  R  V  L  D  L  S  F  T  S  I  -
b       Q  G  F  S  C  I  C  L  F  S  E  S  W  T  C  R  S  Q  V  S  -
c        R  V  F  H  A  Y  A  C  S  Q  S  L  G  L  V  V  H  K  Y  H -

ACTGAGATTCCGTTGTCTATCAAGTATTTGGTGGAGTTGTATCATCTGTCTATGTCAGGA
1741  ------------------------------------------------------------  1800
      TGACTCTAAGGCAACAGATAGTTCATAAACCACCTCAACATAGTAGACAGATACAGTCCT a      T  E  I  P  L  S  I  K  Y  L  V  E  L  Y  H  L  S  M  S  G  -
b       L  R  F  R  C  L  S  S  I  W  W  S  C  I  I  C  L  C  Q  E  -
c        *  D  S  V  V  Y  Q  V  F  G  G  V  V  S  S  V  Y  V  R  N -

ACAAAGATAAGTGTATTGCCACAGGAGCTTGGGAATCTTAGAAAACTGAAGCATCTGGAC
1801  ------------------------------------------------------------  1860
      TGTTTCTATTCACATAACGGTGTCCTCGAACCCTTAGAATCTTTTGACTTCGTAGACCTG a      T  K  I  S  V  L  P  Q  E  L  G  N  L  R  K  L  K  H  L  D  -
b       Q  R  *  V  Y  C  H  R  S  L  G  I  L  E  N  *  S  I  W  T  -
c        K  D  K  C  I  A  T  G  A  W  E  S  *  K  T  E  A  S  G  P -

CTACAAAGAACTCAGTTTCTTCAGACGATCCCACGAGATGCCATATGTTGGCTGAGCAAG
1861  ------------------------------------------------------------  1920
      GATGTTTCTTGAGTCAAAGAAGTCTGCTAGGGTGCTCTACGGTATACAACCGACTCGTTC a      L  Q  R  T  Q  F  L  Q  T  I  P  R  D  A  I  C  W  L  S  K  -
b       Y  K  E  L  S  F  F  R  R  S  H  E  M  P  Y  V  G  *  A  S  -
c        T  K  N  S  V  S  S  D  D  P  T  R  C  H  M  L  A  E  Q  A -

CTCGAGGTTCTGAACTTGTACTACAGTTACGCCGGTTGGGAACTGCAGAGCTTTGGAGAA
1921  ------------------------------------------------------------  1980
      GAGCTCCAAGACTTGAACATGATGTCAATGCGGCCAACCCTTGACGTCTCGAAACCTCTT a      L  E  V  L  N  L  Y  Y  S  Y  A  G  W  E  L  Q  S  F  G  E  -
b       S  R  F  *  T  C  T  T  V  T  P  V  G  N  C  R  A  L  E  K  -
c        R  G  S  E  L  V  L  Q  L  R  R  L  G  T  A  E  L  W  R  R -

GATGAAGCAGAAGAACTCGGATTCGCTGACTTGGAATACTTGGAAAACCTAACCACACTC
1981  ------------------------------------------------------------  2040
      CTACTTCGTCTTCTTGAGCCTAAGCGACTGAACCTTATGAACCTTTTGGATTGGTGTGAG
```

GGTATCACTGTTCTCTCATTGGAGACCCTAAAAACTCTCTTCGAGTTCGGTGCTTTGCAT
2041   ---------+---------+---------+---------+---------+---------+ 2100
       CCATAGTGACAAGAGAGTAACCTCTGGGATTTTTGAGAGAAGCTCAAGCCACGAAACGTA a      G I T V L S L E T L K T L F E F G A L H  -
b       V S L F S H W R P * K L S S S S V L C I -
c        Y H C S L I G D P K N S L R V R C F A * -

AAACATATACAGCATCTCCACGTTGAAGAGTGCAATGAACTCCTCTACTTCAATCTCCCA
2101   ---------+---------+---------+---------+---------+---------+ 2160
       TTTGTATATGTCGTAGAGGTGCAACTTCTCACGTTACTTGAGGAGATGAAGTTAGAGGGT a      K H I Q H L H V E E C N E L L Y F N L P  -
b       N I Y S I S T L K S A M N S S T S I S H -
c        T Y T A S P R * R V Q * T P L L Q S P I -

TCACTCACTAACCATGGCAGGAACCTGAGAAGACTTAGCATTAAAAGTTGCCATGACTTG
2161   ---------+---------+---------+---------+---------+---------+ 2220
       AGTGAGTGATTGGTACCGTCCTTGGACTCTTCTGAATCGTAATTTTCAACGGTACTGAAC a      S L T N H G R N L R R L S I K S C H D L  -
b       H S L T M A G T * E D L A L K V A M T W -
c        T H * P W Q E P E K T * H * K L P * L G -

GAGTACCTGGTCACACCCGCAGATTTTGAAAATGATTGGCTTCCGAGTCTAGAGGTTCTG
2221   ---------+---------+---------+---------+---------+---------+ 2280
       CTCATGGACCAGTGTGGGCGTCTAAAACTTTTACTAACCGAAGGCTCAGATCTCCAAGAC a      E Y L V T P A D F E N D W L P S L E V L  -
b       S T W S H P Q I L K M I G F R V * R F * -
c        V P G H T R R F * K * L A S E S R G S D -

ACGTTACACAGCCTTCACAACTTAACCAGAGTGTGGGGAAATTCTGTAAGCCAAGATTGT
2281   ---------+---------+---------+---------+---------+---------+ 2340
       TGCAATGTGTCGGAAGTGTTGAATTGGTCTCACACCCCTTTAAGACATTCGGTTCTAACA a      T L H S L H N L T R V W G N S V S Q D C  -
b       R Y T A F T T * P E C G E I L * A K I V -
c        V T Q P S Q L N Q S V G K F C K P R L S -

CTGCGGAATATCCGTTGCATAAACATTTCACACTGCAACAAGCTGAAGAATGTCTCATGG
2341   ---------+---------+---------+---------+---------+---------+ 2400
       GACGCCTTATAGGCAACGTATTTGTAAAGTGTGACGTTGTTCGACTTCTTACAGAGTACC a      L R N I R C I N I S H C N K L K N V S W  -
b       C G I S V A * T F H T A T S * R M S H G -
c        A E Y P L H K H F T L Q Q A E E C L M G -

GTTCAGAAACTCCCAAAGCTAGAGGTGATTGAACTGTTCGACTGCAGAGAGATAGAGGAA
2401   ---------+---------+---------+---------+---------+---------+ 2460
       CAAGTCTTTGAGGGTTTCGATCTCCACTAACTTGACAAGCTGACGTCTCTCTATCTCCTT
```

TTGATAAGCGAACACGAGAGTCCATCCGTCGAAGATCCAACATTGTTCCCAAGCCTGAAG
2461    ---------+---------+---------+---------+---------+---------+ 2520
        AACTATTCGCTTGTGCTCTCAGGTAGGCAGCTTCTAGGTTGTAACAAGGGTTCGGACTTC a    L  I  S  E  H  E  S  P  S  V  E  D  P  T  L  F  P  S  L  K    -
b       *  *  A  N  T  R  V  H  P  S  K  I  Q  H  C  S  Q  A  *  R  -
c          D  K  R  T  R  E  S  I  R  R  R  S  N  I  V  P  K  P  E  D -

ACCTTGAGAACTAGGGATCTGCCAGAACTAAACAGCATCCTCCCATCTCGATTTTCATTC
2521    ---------+---------+---------+---------+---------+---------+ 2580
        TGGAACTCTTGATCCCTAGACGGTCTTGATTTGTCGTAGGAGGGTAGAGCTAAAAGTAAG a    T  L  R  T  R  D  L  P  E  L  N  S  I  L  P  S  R  F  S  F    -
b       P  *  E  L  G  I  C  Q  N  *  T  A  S  S  H  L  D  F  H  S  -
c          L  E  N  *  G  S  A  R  T  K  Q  H  P  P  I  S  I  F  I  P -

CAAAAAGTTGAAACATTAGTCATCACAAATTGCCCCAGAGTTAAGAAACTGCCGTTTCAG
2581    ---------+---------+---------+---------+---------+---------+ 2640
        GTTTTTCAACTTTGTAATCAGTAGTGTTTAACGGGGTCTCAATTCTTTGACGGCAAAGTC a    Q  K  V  E  T  L  V  I  T  N  C  P  R  V  K  K  L  P  F  Q    -
b       K  K  L  K  H  *  S  S  Q  I  A  P  E  L  R  N  C  R  F  R  -
c          K  S  *  N  I  S  H  H  K  L  P  Q  S  *  E  T  A  V  S  G -

GAGAGGAGGACCCAGATGAACTTGCCAACAGTTTATTGTGAGGAGAAATGGTGGAAAGCA
2641    ---------+---------+---------+---------+---------+---------+ 2700
        CTCTCCTCCTGGGTCTACTTGAACGGTTGTCAAATAACACTCCTCTTTACCACCTTTCGT a    E  R  R  T  Q  M  N  L  P  T  V  Y  C  E  E  K  W  W  K  A    -
b       R  G  G  P  R  *  T  C  Q  Q  F  I  V  R  R  N  G  G  K  H  -
c          E  E  D  P  D  E  L  A  N  S  L  L  *  G  E  M  V  E  S  T -

CTGGAAAAAGATCAACCAAACGAAGAGCTTTGTTATTTACCGCGCTTTGTTCCAAATTGA
2701    ---------+---------+---------+---------+---------+---------+ 2760
        GACCTTTTTCTAGTTGGTTTGCTTCTCGAAACAATAAATGGCGCGAAACAAGGTTTAACT a    L  E  K  D  Q  P  N  E  E  L  C  Y  L  P  R  F  V  P  N  *    -
b       W  K  K  I  N  Q  T  K  S  F  V  I  Y  R  A  L  F  Q  I  D  -
c          G  K  R  S  T  K  R  R  A  L  L  F  T  A  L  C  S  K  L  I -

TATAAGAGCTAAGAGCACTCTGTACAAATATGTCCATTCATAAGATGCAGGAAGCCAGGA
2761    ---------+---------+---------+---------+---------+---------+ 2820
        ATATTCTCGATTCTCGTGAGACATGTTTATACAGGTAAGTATTCTACGTCCTTCGGTCCT a    Y  K  S  *  E  H  S  V  Q  I  C  P  F  I  R  C  R  K  P  G    -
b       I  R  A  K  S  T  L  Y  K  Y  V  H  S  *  D  A  G  S  Q  E  -
c          *  E  L  R  A  L  C  T  N  M  S  I  H  K  M  Q  E  A  R  K -

AGGTTGTTCCAGTGAAGTCATCAACTTTCCACATAGCCACAAAACTAGAGATTATGTAAT
2821    ---------+---------+---------+---------+---------+---------+ 2880
        TCCAACAAGGTCACTTCAGTAGTTGAAAGGTGTATCGGTGTTTTGATCTCTAATACATTA
```

CATAAAAACCAAACTATCCGCGA
2881    ---------+---------+--- 2903
        GTATTTTTGGTTTGATAGGCGCT a    H  K  N  Q  T  I  R      -
b     I  K  T  K  L  S  A     -
c      *  K  P  N  Y  P  R    -
```

ENZYMES THAT DO CUT:

NONE

ENZYMES THAT DO NOT CUT:

KpnI

Fig. 2H

```
-146
ATCGATTGATCTCTGGCTCAGTGCGAGTAGTCCATTTGAGAGCAGTCGTAGCCCCGCGTG    -86

GCGCATCATGGAGCTATTTGGAATTTTCGCAGGGTTATCGATTCGTAGTGGGAACCCATT    -26
                                1
CATTGTTTGGAACCACCAACGGACGACTTAACAAGCTCCCCGAGGTGCATGATGAAAATT     35
                                         MetLysIle

GCTCCAGTTGCCATAAATCACAGCCCGCTCAGCAGGGAGGTCCCGTCACACGCGGCACCC     95
AlaProValAlaIleAsnHisSerProLeuSerArgGluValProSerHisAlaAlaPro

ACTCAGGCAAAGCAAACCAACCTTCAATCTGAAGCTGGCGATTTAGATGCAAGAAAAAGT    155
ThrGlnAlaLysGlnThrAsnLeuGlnSerGluAlaGlyAspLeuAspAlaArgLysSer

AGCGCTTCAAGCCCGGAAACCCGCGCATTACTCGCTACTAAGACAGTACTCGGGAGACAC    215
SerAlaSerSerProGluThrArgAlaLeuLeuAlaThrLysThrValLeuGlyArgHis

AAGATAGAGGTTCCGGCCTTTGGAGGGTGGTTCAAAAAGAAATCATCTAAGCACGAGACG    275
LysIleGluValProAlaPheGlyGlyTrpPheLysLysLysSerSerLysHisGluThr

GGCGGTTCAAGTGCCAACGCAGATAGTTCGAGCGTGGCTTCCGATTCCACCGAAAAACCT    335
GlyGlySerSerAlaAsnAlaAspSerSerSerValAlaSerAspSerThrGluLysPro

TTGTTCCGTCTCACGCACGTTCCTTACGTATCCCAAGGTAATGAGCGAATGGGATGTTGG    395
LeuPheArgLeuThrHisValProTyrValSerGlnGlyAsnGluArgMetGlyCysTrp

TATGCCTGCGCAAGAATGGTTGGCCATTCTGTCGAAGCTGGGCCTCGCCTAGGGCTGCCG    455
TyrAlaCysAlaArgMetValGlyHisSerValGluAlaGlyProArgLeuGlyLeuPro

GAGCTCTATGAGGGAAGGGAGGCGCCAGCTGGGCTACAAGATTTTTCAGATGTAGAAAGG    515
GluLeuTyrGluGlyArgGluAlaProAlaGlyLeuGlnAspPheSerAspValGluArg

TTTATTCACAATGAAGGATTAACTCGGGTAGACCTTCCAGACAATGAGAGATTTACACAC    575
PheIleHisAsnGluGlyLeuThrArgValAspLeuProAspAsnGluArgPheThrHis
```

Fig. 3A

```
GAAGAGTTGGGTGCACTGTTGTATAAGCACGGGCCGATTATATTTGGGTGGAAAACTCCG   635
GluGluLeuGlyAlaLeuLeuTyrLysHisGlyProIleIlePheGlyTrpLysThrPro

AATGACAGCTGGCACATGTCGGTCCTCACTGGTGTCGATAAAGAGACGTCGTCCATTACT   695
AsnAspSerTrpHisMetSerValLeuThrGlyValAspLysGluThrSerSerIleThr

TTTCACGATCCCCGACAGGGGCCGGACCTAGCAATGCCGCTCGATTACTTTAATCAGCGA   755
PheHisAspProArgGlnGlyProAspLeuAlaMetProLeuAspTyrPheAsnGlnArg

TTGGCATGGCAGGTTCCACACGCAATGCTCTACCGCTAAGTAGCAGGGTATCTTCACGTG   815
LeuAlaTrpGlnValProHisAlaMetLeuTyrArgEnd

GCGGCATCATGACAAGCCCATGATGCCGCCAGCAGCTACCTGAATGCCGTCTGGCTTTTT   875
    ──────────────▶  ◀──────

GGTCCCTATTGTCGTATCCGGAAGATGACGTCAAAGAATCTCGGCAAGAGCTTTCTTGCT   935

CGACTCCTCAGCTTCCGGATCGATCAGGTCGCTTGCCAGAGCGCGCTTGTCCATGAGCAT   995

CTGCCACAGCTGCTGGTCGATGGTGTCCTCAGCTAAAGGGATTTTGACGACAACCATGCG  1055

CAACTGCCCGTTGCGATACGCTCGATCCTGAAGCCCCGGTGTCCATGGCAGCCCCAAGAA  1115

AAAGACATAGTTCGCCGCTGTGAGGTTGTAGCCTGTGCCGGCGGCCGACCTGGTCCCGAT  1175

AAACACCCTGCAGTCCGGATCCTGCTGGAAAGCATCAATCGCCTTCTGCCGCTTCTTGGG  1235

CGAGTCACTGCCCACCAACGTCACGCACCCGACGCCAAGCTTGAGGCAGTGCTCCCGCAA  1295

CGTGGCCACGGATTCCTGATACTCGCAGAAGAGGATCACCTTGTCGTCGAC   1346
```

Fig. 3B

PLANT RESISTANCE GENE FAMILY ENCODING RESISTANCE POLYPEPTIDES HAVING P-LOOP AND LRR MOTIFS

This is a continuation of application Ser. No. 08/227,360, filed Apr. 13, 1994, now abandoned.

This invention was made with Government support under Contract #GM 48707 awarded by the National Institutes of Health. The Government has certain rights in the invention.

BACKGROUND OF THE INVENTION

The invention relates to recombinant plant nucleic acids and polypeptides and uses thereof to confer disease resistance to pathogens in transgenic plants.

Plants employ a variety of defensive strategies to combat pathogens. One defense response, the so-called hypersensitive response (HR), involves rapid localized necrosis of infected tissue. In several host-pathogen interactions, genetic analysis has revealed a gene-for-gene correspondence between a particular avirulence (avr) gene in an avirulent pathogen that elicits an HR in a host possessing a particular resistance gene.

SUMMARY OF THE INVENTION

In general, the invention features substantially pure DNA (for example, genomic DNA, cDNA or synthetic DNA) encoding an Rps polypeptide as defined below. In related aspects, the invention also features a vector, a cell (e.g., a plant cell), and a transgenic plant or seed thereof which includes such a substantially pure DNA encoding an Rps polypeptide.

In preferred embodiments, an RPS gene is the RPS2 gene (SEQ ID NO: 2) of a plant of the genus Arabidopsis. In various preferred embodiments, the cell is a transformed plant cell derived from a cell of a transgenic plant. In related aspects, the invention features a transgenic plant containing a transgene which encodes an Rps polypeptide that is expressed in plant tissue susceptible to infection by pathogens expressing the avrRpt2 avirulence (SEQ ID NO: 105) gene or pathogens expressing an avirulence signal similarly recognized by an Rps polypeptide.

In a second aspect, the invention features a substantially pure DNA which includes a promoter capable of expressing the RPS2 (SEQ ID NO: 2) gene in plant tissue susceptible to infection by bacterial pathogens expressing the avrRpt2 avirulence (SEQ ID NO: 105) gene.

In preferred embodiments, the promoter is the promoter native to an RPS gene. Additionally, transcriptional and translational regulatory regions are preferably native to an RPS gene.

The transgenic plants of the invention are preferably plants which are susceptible to infection by a pathogen expressing an avirulence gene, preferably the avrRpt2 avirulence gene (SEQ ID NO: 105). In preferred embodiments the transgenic plant is from the group of plants consisting of but not limited to Arabidopsis, tomato, soybean, bean, maize, wheat and rice.

In another aspect, the invention features a method of providing resistance in a plant to a pathogen which involves: (a) producing a transgenic plant cell having a transgene encoding an Rps2 polypeptide wherein the transgene is integrated into the genome of the transgenic plant and is positioned for expression in the plant cell; and (b) growing a transgenic plant from the transgenic plant cell wherein the RPS2 transgene is expressed in the transgenic plant.

In another aspect, the invention features a method of detecting a resistance gene in a plant cell involving: (a) contacting the RPS2 (SEQ ID NO: 2) gene or a portion thereof greater than 18 nucleic acids in length with a preparation of genomic DNA from said plant cell under hybridization conditions providing detection of DNA sequences having about 50% or greater sequence identity to the DNA sequence of FIG. 2 encoding the Rps2 polypeptide (SEQ ID NOS: 2–5).

In another aspect, the invention features a method of producing an Rps2 polypeptide which involves: (a) providing a cell transformed with DNA encoding an Rps2 polypeptide positioned for expression in the cell; (b) culturing the transformed cell under conditions for expressing the DNA; and (c) isolating the Rps2 polypeptide.

In another aspect, the invention features substantially pure Rps2 polypeptide. Preferably, the polypeptide includes a greater than 50 amino acid sequence substantially identical to a greater than 50 amino acid sequence shown in FIG. 2, open reading frame "a". Most preferably, the polypeptide is the *Arabidopsis thaliana* Rps2 polypeptide (SEQ ID NOS: 2–5).

In another aspect, the invention features a method of providing resistance in a transgenic plant to infection by pathogens which do not carry the avrRpt2 avirulence gene wherein the method includes: (a) producing a transgenic plant cell having transgenes encoding an Rps2 polypeptide as well as a transgene encoding the avrRpt2 gene product (SEQ ID NO: 106) wherein the transgenes are integrated into the genome of the transgenic plant; are positioned for expression in the plant cell; and the avrRpt2 transgene and, if desired, the RPS2 gene, are under the control of regulatory sequences suitable for controlled expression of the gene(s); and (b) growing a transgenic plant from the transgenic plant cell wherein the RPS2 and avrRpt2 transgenes are expressed in the transgenic plant.

In another aspect, the invention features a method of providing resistance in a transgenic plant to infection by pathogens in the absence of avirulence gene expression in the pathogen wherein the method involves: (a) producing a transgenic plant cell having integrated in the genome a transgene containing the RPS2 gene under the control of a promoter providing constitutive expression of the RPS2 gene; and (b) growing a transgenic plant from the transgenic plant cell wherein the RPS2 transgene is expressed constitutively in the transgenic plant.

In another aspect, the invention features a method of providing controllable resistance in a transgenic plant to infection by pathogens in the absence of avirulence gene expression in the pathogen wherein the method involves: (a) producing a transgenic plant cell having integrated in the genome a transgene containing the RPS2 gene under the control of a promoter providing controllable expression of the RPS2 gene; and (b) growing a transgenic plant from the transgenic plant cell wherein the RPS2 transgene is controllably expressed in the transgenic plant. In preferred embodiments, the RPS2 gene is expressed using a tissue-specific or cell type-specific promoter, or by a promoter that is activated by the introduction of an external signal or agent, such as a chemical signal or agent.

By "disease resistance gene" is meant a gene encoding a polypeptide capable of triggering the plant defense response in a plant cell or plant tissue. An RPS gene is a disease resistance gene having about 50% or greater sequence identity to the RPS2 (SEQ ID NO: 2) sequence of FIG. 2 or a portion thereof. The gene, RPS2, is a disease resistance gene encoding the Rps2 disease resistance polypeptide (SEQ ID NOS: 2–5) from *Arabidopsis thaliana*.

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

By a "substantially pure polypeptide" is meant an Rps2 polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, Rps2 polypeptide. A substantially pure Rps2 polypeptide may be obtained, for example, by extraction from a natural source (e.g., a plant cell); by expression of a recombinant nucleic acid encoding an Rps2 polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) an Rps2 polypeptide.

By "positioned for expression" is meant that the DNA molecule is positioned adjacent to a DNA sequence which directs transcription and translation of the sequence (i.e., facilitates the production of, e.g., an Rps2 polypeptide, a recombinant protein or a RNA molecule).

By "reporter gene" is meant a gene whose expression may be assayed; such genes include, without limitation, β-glucuronidase (GUS), luciferase, chloramphenicol transacetylase (CAT), and β-galactosidase.

By "promoter" is meant minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "operably linked" is meant that a gene and a regulatory sequence(s) are connected in such a way as to permit gene expression when the appropriate molecules (e.g., transcriptional activator proteins) are bound to the regulatory sequence(s).

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds suspension cultures, embryos, meristematic regions, callus tissue, leaves, roots, shoots, gametophytes, sporophytes, pollen, and microspores.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic plants and the DNA (transgene) is inserted by artifice into the nuclear or plastidic genome.

By "pathogen" is meant an organism whose infection into the cells of viable plant tissue elicits a disease response in the plant tissue.

Other features and advantages of the invention will be apparent from the following description of the preferred embodiments thereof, and from the claims.

DETAILED DESCRIPTION OF THE INVENTION

The drawings will first be described.

Drawings

FIGS. 1A–1F are a schematic summary of the physical and RFLP analysis that led to the cloning of the RPS2 locus.

FIG. 1A is a diagram showing the alignment of the genetic and the RFLP maps of the relevant portion of *Arabidopsis thaliana* chromosome IV adapted from the map published by Lister and Dean (1993) Plant J. 4:745–750. The RFLP marker L11F11 represents the left arm of the YUP11F11 YAC clone.

Figure 4:
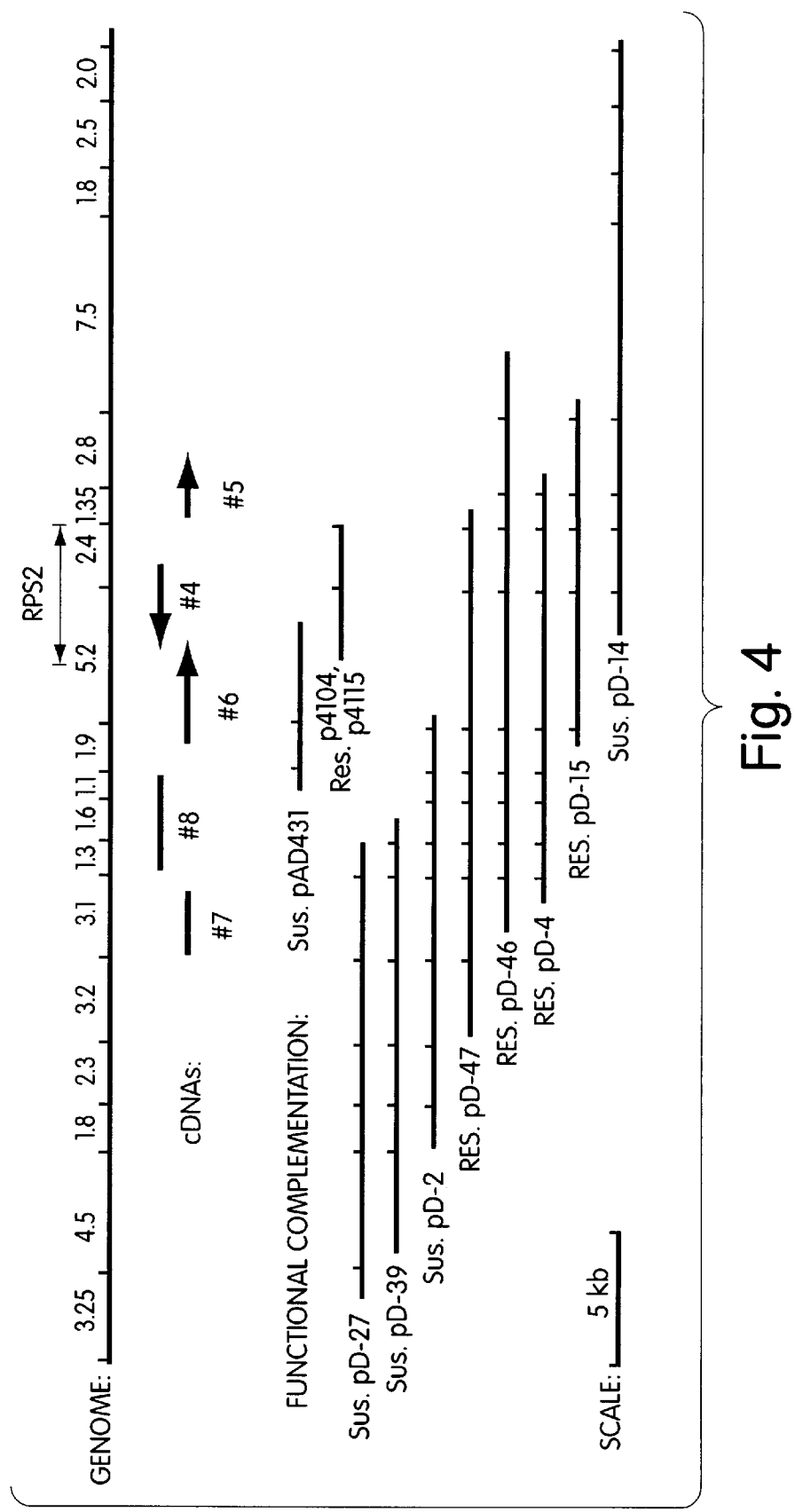

FIG. 1B is a diagram showing the alignment of relevant YACs around the RPS2 locus. YAC constructs designated YUP16G5, YUP18G9 and YUP11F11were provided by J. Ecker, University of Pennsylvania. YAC constructs designated EW3H7, EW11D4, EW11E4, and EW9C3 were provided by E. Ward, Ciba-Geigy, Inc.

FIG. 1C is a diagram showing the alignment of cosmid clones around the RPS2 locus. Cosmid clones with the designation H are derivatives of the EW3H7 YAC clone whereas those with the designation E are derivatives of the EW11E4 YAC clone. Vertical arrows indicate the relative positions of RFLP markers between the ecotypes La-er and the rps2-101N plant. The RFLP markers were identified by screening a Southern blot containing more than 50 different restriction enzyme digests using either the entire part or pieces of the corresponding cosmid clones as probes. The cosmid clones described in FIG. 1C were provided by J. Giraudat, C. N. R. S., Gif-sur-Yvette, France.

FIGS. 1D and 1E are maps of EcoRI restriction endonuclease sites in the cosmids E4-4 and E4-6, respectively. The recombination break points surrounding the RPS2 locus are located within the 4.5 and 7.5 kb EcoRI restriction endonuclease fragments.

FIG. 1F is a diagram showing the approximate location of genes which encode the RNA transcripts which have been identified by polyA$^+$ RNA blot analysis. The sizes of the transcripts are given in kilobase pairs below each transcript.

FIGS. 2A–2G are is the complete nucleotide sequence of cDNA-4 comprising the RPS2 (SEQ ID NO: 2) gene locus. The three reading frames are shown below the nucleotide sequence. The deduced amino acid sequence (SEQ ID NOS: 2–5) of reading frame "a" is provided and contains 909 amino acids. The methionine encoded by the ATG start codon is circled in open reading frame "a" of FIG. 2. The A of the ATG start codon is nucleotide 31 of FIG. 2.

FIGS. 3A–3B are is the nucleotide sequence of the avrRpt2 gene (SEQ ID NO: 105) and its deduced amino acid sequence (SEQ ID NO: 106). A potential ribosome binding site is underlined. An inverted repeat is indicated by horizontal arrows at the 3' end of the open reading frame. The deduced amino acid sequence is provided below the nucleotide sequence of the open reading frame.

FIG. 4 is a schematic summary of the complementation analysis that allowed functional confirmation that the DNA carried on p4104 and p4115 (encoding cDNA-4) confers RPS2 disease resistance activity to *Arabidopsis thaliana* plants previously lacking RPS2 disease resistance activity. Small vertical marks along the "genome" line represent restriction enzyme EcoRI recognition sites, and the numbers above this line represent the size, in kilobasepairs (kb), of the resulting DNA fragments (see also FIG. 1E). Opposite "cDNAs" are the approximate locations of the coding sequences for RNA transcripts (See also FIG. 1F); arrowheads indicate the direction of transcription for cDNAs 4, 5, and 6. For functional complementation experiments, rps2-201C/rps2-201C plants were genetically transformed with the *Arabidopsis thaliana* genomic DNA sequences indicated; these sequences were carried on the named plasmids (derivatives of the binary cosmid vector pSLJ4541) and delivered to the plant via Agrobacterium-mediated transformation methods.

The disease resistance phenotype of the resulting transformants following inoculation with *P. syringae* expressing avrRpt2 is given as "Sus." (susceptible, no resistance response) or "Res." (disease resistant).

The Genetic Basis for Resistance to Pathogens

An overview of the interaction between a plant host and a microbial pathogen is presented. The invasion of a plant by a potential pathogen can have a range of outcomes delineated by the following outcomes: either the pathogen successfully proliferates in the host, causing associated disease symptoms, or its growth is halted by the host defenses. In some plant-pathogen interactions, the visible hallmark of an active defense response is the so-called hypersensitive response or "HR". The HR involves rapid necrosis of cells near the site of the infection and may include the formation of a visible dry brown lesion. Pathogens which elicit an HR on a given host are said to be avirulent on that host, the host is said to be resistant, and the plant-pathogen interaction is said to be incompatible. Strains which proliferate and cause disease on a particular host are said to be virulent; in this case the host is said to be susceptible, and the plant-pathogen interaction is said to be compatible "Classical" genetic analysis has been used successfully to help elucidate the genetic basis of plant-pathogen recognition for those cases in which a series of strains (races) of a particular fungal or bacterial pathogen are either virulent or avirulent on a series of cultivars (or different wild accessions) of a particular host species. In many such cases, genetic analysis of both the host and the pathogen revealed that many avirulent fungal and bacterial strains differ from virulent ones by the possession of one or more avirulence (avr) genes that have corresponding "resistance" genes in the host. This avirulence gene-resistance gene correspondence is termed the "gene-for-gene" model (Crute, et al., (1985) pp 197–309 in: *Mechanisms of Resistance to Plant Disease*. R. S. S. Fraser, ed.; Ellingboe, (1981) Annu. Rev. Phytopathol. 19:125–143; Flor, (1971) Annu. Rev. Phytopathol. 9:275–296; Keen and Staskawicz, (1988) supra; and Keen et al. in: *Application of Biotechnology to Plant Pathogen Control*. I. Chet, ed., John Wiley & Sons, 1993, pp. 65–88). According to a simple formulation of this model, plant resistance genes encode specific receptors for molecular signals generated by avr genes. Signal transduction pathway(s) then carry the signal to a set of target genes that initiate the HR and other host defenses (Gabriel and Rolfe, (1990) Annu. Rev. Phytopathol. 28:365–391). Despite this simple predictive model, the molecular basis of the avr-resistance gene interaction is still unknown.

One basic prediction of the gene-for-gene hypothesis has been convincingly confirmed at the molecular level by the cloning of a variety of bacterial avr genes (Innes, et al., (1993) J. Bacteriol. 175:4859–4869; Dong, et al., (1991) Plant Cell 3:61–72; Whelan et al., (1991) Plant Cell 3:49–59; Staskawicz et al., (1987) J. Bacteriol. 169:5789–5794; Gabriel et al., (1986) P.N.A.S., USA 83:6415–6419; Keen and Staskawicz, (1988) Annu. Rev. Microbiol. 42:421–440; Kobayashi et al., (1990) Mol. Plant-Microbe Interact. 3:94–102 and (1990) Mol. Plant-Microbe Interact. 3:103–111). Many of these cloned avirulence genes have been shown to correspond to individual resistance genes in the cognate host plants and have been shown to confer an avirulent phenotype when transferred to an otherwise virulent strain. The avrRpt2 locus was isolated from *Pseudomonas syringae* pv. *tomato* and sequenced by Innes et al. (Innes, R. et al. (1993) J. Bacteriol. 175:4859–4869). FIG. 3 is the nucleotide sequence (SEQ ID NO: 105) and deduced amino acid sequence (SEQ ID NO: 106) of the avrRpt2 gene.

Examples of known signals to which plants respond when infected by pathogens include harpins from Erwinia (Wei et al. (1992) Science 257:85–88) and Pseudomonas (He et al. (1993) Cell 73:1255–1266); avr4 (Joosten et al. (1994) Nature 367:384–386) and avr9 peptides (van den Ackerveken et al (1992) Plant J. 2:359–366) from Cladosporium; PopA1 from Pseudomonas (Arlat et al. (1994) EMBO J. 13:543–553); avrD-generated lipopolysaccharide (Midland et al. (1993) J. Org. Chem. 58:2940–2945); and NIP1 from Rhynchosporium (Hahn et al. (1993) Mol. Plant-Microbe Interact. 6:745–754).

Compared to avr genes, considerably less is known about plant resistance genes that correspond to specific avr-generated signals. The plant resistance gene, RPS2 (rps for resistance to Pseudomonas syringae), the first gene of a new, previously unidentified class of plant disease resistance genes corresponds to a specific avr gene (avrRpt2). Some of the work leading up to the cloning of RPS2 is described in Yu, et al., (1993), Molecular Plant-Microbe Interactions 6:434–443 and in Kunkel, et al., (1993) Plant Cell 5:865–875.

An apparently unrelated avirulence gene which corresponds specifically to plant disease resistance gene, Pto, has been isolated from tomato (Lycopersicon esculentum) (Martin et al., (1993) Science 262:1432–1436). Tomato plants expressing the Pto gene are resistant to infection by strains of Pseudomonas syringae pv. tomato that express the avrPto avirulence gene. The amino acid sequence inferred from the Pto gene DNA sequence displays strong similarity to serine-threonine protein kinases, implicating Pto in signal transduction. No similarity to the tomato Pto locus or any known protein kinases was observed for RPS2, suggesting that RPS2 is representative of a new class of plant disease resistance genes.

The isolation of a race-specific resistance gene from Zea mays (corn) known as Hm1 has been reported (Johal and Briggs (1992) Science 258:985–987). Hm1 confers resistance against specific races of the fungal pathogen Cochliobolus carbonum by controlling degradation of a fungal toxin, a strategy that is mechanistically distinct from the avirulence-gene specific resistance of the RPS2-avrRpt2 resistance mechanism.

The cloned RPS2 gene of the invention can be used to facilitate the construction of plants that are resistant to specific pathogens and to overcome the inability to transfer disease resistance genes between species using classical breeding techniques (Keen et al., (1993), supra). There now follows a description of the cloning and characterization of an Arabidopsis thaliana RPS2 genetic locus, the RPS2 genomic DNA, and the RPS2 cDNA. The avrRpt2 gene and the RPS2 gene, as well as mutants rps2-101C, rps2-102C, and rps2-201C (also designated rps2-201), are described in Dong, et al., (1991) Plant Cell 3:61–72; Yu, et al., (1993) supra; Kunkel et al., (1993) supra; Whalen et al., (1991), supra; and Innes et al., (1993), supra). A mutant designated rps2-101N has also been isolated. The identification and cloning of the RPS2 gene is described below.

RPS2 Overcomes Sensitivity to Pathogens Carrying the avrRpt2 Gene.

To demonstrate the genetic relationship between an avirulence gene in the pathogen and a resistance gene in the host, it was necessary first to isolate an avirulence gene. By screening Pseudomonas strains that are known pathogens of crop plants related to Arabidopsis, highly virulent strains, P. syringae pv. maculicola (Psm) ES4326, P. syringae pv. tomato (Pst) DC3000, and an avirulent strain, Pst MM1065 were identified and analyzed as to their respective abilities to grow in wild type Arabidopsis thaliana plants (Dong et al., (1991) Plant Cell, 3:61–72; Whalen et al., (1991) Plant Cell 3:49–59; MM1065 is designated JL1065 in Whalen et al.). Psm ES4326 or Pst DC3000 can multiply 104 fold in Arabidopsis thaliana leaves and cause water-soaked lesions that appear over the course of two days. Pst MM1065 multiplies a maximum of 10 fold in Arabidopsis thaliana leaves and causes the appearance of a mildly chlorotic dry lesion after 48 hours. Thus, disease resistance is associated with severely inhibited growth of the pathogen.

An avirulence gene (avr) of the Pst MM1065 strain was cloned using standard techniques as described in Dong et al. (1991), Plant Cell 3:61–72; Whalen et al., (1991) supra; and Innes et al., (1993), supra. The isolated avirulence gene from this strain was designated avrRpt2. Normally, the virulent strain Psm ES4326 or Pst DC3000 causes the appearance of disease symptoms after 48 hours as described above. In contrast, Psm ES4326/avrRpt2 or Pst DC3000/avrRpt2 elicits the appearance of a visible necrotic hypersensitivity response (HR) within 16 hours and multiplies 50 fold less than Psm ES4326 or Pst DC3000 in wild type Arabidopsis thaliana leaves (Dong et al., (1991), supra; and Whalen et al., (1991), supra). Thus, disease resistance in a wild type Arabidopsis plant requires, in part, an avirulence gene in the pathogen or a signal generated by the avirulence gene.

The isolation of four Arabidopsis thaliana disease resistance mutants has been described using the cloned avrRpt2 gene to search for the host gene required for disease resistance to pathogens carrying the avrRpt2 gene (Yu et al., (1993), supra; Kunkel et al., (1993), supra). The four Arabidopsis thaliana mutants failed to develop an HR when infiltrated with Psm ES4326/avrRpt2 or Pst DC3000/avrRpt2 as expected for plants having lost their disease resistance capacity. In the case of one of these mutants, approximately 3000 five to six week old $M_2$ ecotype Columbia (Col-O plants) plants generated by ethyl methanesulfonic acid (EMS) mutagenesis were hand-inoculated with Psm ES4326/avrRpt2 and a single mutant, rps2-101C, was identified (resistance to Pseudomonas syringae) (Yu et al., (1993), supra).

The second mutant was isolated using a procedure that specifically enriches for mutants unable to mount an HR (Yu et al., (1993), supra). When 10-day old Arabidopsis thaliana seedlings growing on petri plates are infiltrated with Pseudomonas syringae pv. phaseolicola (Psp) NPS3121 versus Psp NPS3121/avrRpt2, about 90% of the plants infiltrated with Psp NPS3121 survive, whereas about 90%–95% of the plants infiltrated with Psp NPS3121/avrRpt2 die. Apparently, vacuum infiltration of an entire small Arabidopsis thaliana seedling with Psp NPS3121/avrRpt2 elicits a systemic HR which usually kills the seedling. In contrast, seedlings infiltrated with Psp NPS3121 survive because Psp NPS3121 is a weak pathogen on Arabidopsis thaliana. The second disease resistance mutant was isolated by infiltrating 4000 EMS-mutagenized Columbia $M_2$ seedlings with Psp NPS3121/avrRpt2. Two hundred survivors were obtained. These were transplanted to soil and re-screened by hand inoculation when the plants reached maturity of these 200 survivors, one plant failed to give an HR when hand-infiltrated with Psm ES4326/avrRpt2. This mutant was designated rps2-102C (Yu et al., (1993), surra).

A third mutant, rps2-201C, was isolated in a screen of approximately 7500 $M_2$ plants derived from seed of Arabidopsis thaliana ecotype Col-O that had been mutagenized with diepoxybutane (Kunkel et al., (1993), supra). Plants were inoculated by dipping entire leaf rosettes into a solution containing Pst DC3000/avrRpt2 bacteria and the surfactant Silwet L-77 (Whalen et al., (1991), supra), incubating plants in a controlled environment growth chamber for three to four days, and then visually observing disease symptom development. This screen revealed four mutant lines (carrying the rps2-201C, rps2-202C, rps2-203C, and rps2-204C alleles), and plants homozygous for rps2-201C were a primary subject for further study (Kunkel et al., (1993), supra and the instant application).

Isolation of the fourth rps2 mutant, rps2-101N, has not yet been published. This fourth isolate is either a mutant or a susceptible Arabidopsis ecotype. Seeds of the Arabidopsis Nossen ecotype were gamma-irradiated and then sown densely in flats and allowed to germinate and grow through a nylon mesh. When the plants were five to six weeks old, the flats were inverted, the plants were partially submerged in a tray containing a culture of Psm ES4326/avrRpt2, and the plants were vacuum infiltrated in a vacuum desiccator. Plants inoculated this way develop an HR within 24 hours. Using this procedure, approximately 40,000 plants were screened and one susceptible plant was identified. Subsequent RFLP analysis of this plant suggested that it may not be a Nossen mutant but rather a different Arabidopsis ecotype that is susceptible to Psm ES4326/avrRpt2. This plant is referred to as rps2-101N. The isolated mutants rps2-101C, rps2-102C, rps2-201C, and rps2-101N are referred to collectively as the "rps2 mutants".

The rps2 Mutants Fail to Specifically Respond to the Cloned Avirulence Gene, avrRpt2.

The RPS2 gene product is specifically required for resistance to pathogens carrying the avirulence gene, avrRpt2. A mutation in Rps2 polypeptide that eliminates or reduces its function would be observable as the absence of a hypersensitive response upon infiltration of the pathogen. The rps2 mutants displayed disease symptoms or a null response when infiltrated with Psm ES4326/avrRpt2, Pst DC3000/avrRpt2 or Psp NPS3121/avrRpt2, respectively. Specifically, no HR response was elicited, indicating that the plants were susceptible and had lost resistance to the pathogen despite the presence of the avrRpt2 gene in the pathogen.

Pathogen growth in rps2 mutant plant leaves was similar in the presence and absence of the avrRpt2 gene. Psm ES4326 and Psm ES4326/avrRpt2 growth in rps2 mutants was compared and found to multiply equally well in the rps2 mutants, at the same rate that Psm Es4326 multiplied in wild-type Arabidopsis leaves. Similar results were observed for Pst DC3000 and Pst DC3000/avrRpt2 growth in rps2 mutants.

The rps2 mutants displayed a HR when infiltrated with Pseudomonas pathogens carrying other avr genes, Psm ES4326/avrB, Pst DC3000/avrB, Psm ES4326/avrRpm1, Pst DC3000/avrRpm1. The ability to mount an HR to an avr gene other than avrRpt2 indicates that the rps2 mutants isolated by selection with avrRpt2 are specific to avrRpt2.

Mapping and Cloning of the RPS2 Gene.

Genetic analysis of rps2 mutants rps2-101C, rps2-102C, rps-201C and rps-101N showed that they all corresponded to genes that segregated as expected for a single Mendelian locus and that all four were most likely allelic. The four rps2 mutants were mapped to the bottom of chromosome IV using standard RFLP mapping procedures including polymerase chain reaction (PCR)-based markers (Yu et al., (1993), supra; Kunkel et al., (1993), supra; and Mindrinos, M., unpublished). Segregation analysis showed that rps2-101C and rps2-102C are tightly linked to the PCR marker, PG11, while the RFLP marker M600 was used to define the chromosome location of the rps2-201C mutation (FIG. 1A) (Yu et al., (1993), supra; Kunkel et al., (1993), supra). RPS2 has subsequently been mapped to the centromeric side of PG11.

Heterozygous RPS2/rps2 plants display a defense response that is intermediate between those displayed by the wild-type and homozygous rps2/rps2 mutant plants (Yu, et al., (1993), supra; and Kunkel et al., (1993), supra). The heterozygous plants mounted an HR in response to Psm ES4326/avrRpt2 or Pst DC3000/avrRpt2 infiltration; however, the HR appeared later than in wild type plants and required a higher minimum inoculum (Yu, et al., (1993), supra; and Kunkel et al., (1993), supra).

High Resolution Mapping of the RPS2 Gene and RPS2 cDNA Isolation.

To carry out map-based cloning of the RPS2 gene, rps2-101N/rps2-101N was crossed with Landsberg erecta RPS2/RPS2. Plants of the $F_1$ generation were allowed to self pollinate (to "self") and 165 $F_2$ plants were selfed to generate $F_3$ families. Standard RFLP mapping procedures showed that rps2-101N maps close to and on the centromeric side of the RFLP marker, PG11. To obtain a more detailed map position, rps2-101N/rps-101N was crossed with a doubly marked Landsberg erecta strain containing the recessive mutations, cer2 and ap2. The genetic distance between cer2 and ap2 is approximately 15 cM, and the rps2 locus is located within this interval. $F_2$ plants that displayed either a CER2 ap2 or a cer2 AP2 genotype were collected, selfed, and scored for RPS2 by inoculating at least 20 $F_3$ plants for each $F_2$ with Psm ES4326/avrRpt2. DNA was also prepared from a pool of approximately 20 $F_3$ plants for each $F_2$ line. The CER2 ap2 and cer2 AP2 recombinants were used to carry out a chromosome walk that is illustrated in FIG. 1.

As shown in FIG. 1, RPS2 was mapped to a 28–35 kb region spanned by cosmid clones E4-4 and E4-6. This region contains at least six genes that produce detectable transcripts. There were no significant differences in the sizes of the transcripts or their level of expression in the rps2 mutants as determined by RNA blot analysis. cDNA clones of each of these transcripts were isolated and five of these were sequenced. As is described below, one of these transcripts, cDNA-4, was shown to correspond to the RPS2 locus. From this study, three independent cDNA clones (cDNA-4-4, cDNA-4-5, and cDNA-4-11) were obtained corresponding to RPS2 from Columbia ecotype wild type plants. The apparent sizes of RPS2 transcripts were 3.8 and 3.1 kb as determined by RNA blot analysis.

A fourth independent cDNA-4 clone (cDNA-4-2453) was obtained using map-based isolation of RPS2 in a separate study. Yeast artificial chromosome (YAC) clones were identified that carry contiguous, overlapping inserts of *Arabidopsis thaliana* ecotype Col-O genomic DNA from the M600 region spanning approximately 900 kb in the RPS2 region. Arabidopsis YAC libraries were obtained from J. Ecker and E. Ward, supra and from E. Grill (Grill and Somerville (1991) Mol. Gen. Genet. 226:484–490). Cosmids designated "H" and "E" were derived from the YAC inserts and were used in the isolation of RPS2 (FIG. 1).

The genetic and physical location of RPS2 was more precisely defined using physically mapped RFLP, RAPD (random amplified polymorphic DNA) and CAPS (cleaved amplified polymorphic sequence) markers. Segregating populations from crosses between plants of genotype RPS2/RPS2 (No-O wild type) and rps2-201/rps2-201 (Col-O background) were used for genetic mapping. The RPS2 locus was mapped using markers 17B7LE, PG11, M600 and other markers. For high-resolution genetic mapping, a set of tightly linked RFLP markers was generated using insert end fragments from YAC and cosmid clones (FIG. 1) (Kunkel et al. (1993), supra; Konieczny and Ausubel (1993) Plant J. 4:403–410; and Chang et al. (1988) PNAS USA 85:6856–6860). Cosmid clones E4-4 and E4-6 were then used to identify expressed transcripts (designated cDNA-4, -5, -6, -7, -8 of FIG. 1F) from this region, including the cDNA-4-2453 clone.

RPS2 DNA Sequence Analysis.

DNA sequence analysis of cDNA-4 from wild-type Col-O plants and from mutants rps2-101C, rps2-102C, rps2-201C and rps2-101N showed that cDNA-4 corresponds to RPS2. DNA sequence analysis of rps2-101C, rps2-102C and rps2-201C revealed changes from the wild-type sequence as shown in Table 1. The numbering system in Table 1 starts at the ATG start codon encoding the first methionine where A is nucleotide 1. DNA sequence analysis of cDNA-4 corresponding to mutant rps2-102C showed that it differed from the wild type sequence at amino acid residue 476. Moreover, DNA sequence analysis of the cDNA corresponding to cDNA-4 from rps2-101N showed that it contained a 10 bp insertion at amino acid residue 581, a site within the leucine-rich repeat region which causes a shift in the RPS2 reading frame. Mutant rps2-101C contains a mutation that leads to the formation of a chain termination codon. The DNA sequence of mutant allele rps2-201C revealed a mutation altering a single amino acid within a segment of the LRR region that also has similarity to the helix-loop-helix motif, further supporting the designation of this locus as the RPS2 gene. The DNA and amino acid sequences are shown in FIG. 2.

TABLE 1

| Mutant | Wild type | position of mutation | Change |
|---|---|---|---|
| rps2-101C | 703 TGA 705 | 704 | TAA Stop Codon |
| rps2-101N | 1741 GTG 1743 | 1741 | GTGGAGTTGTATG Insertion |
| rps2-102C | 1426 AGA 1428 arg | 1427 | AAA Amino acid 476 lys |
| rps2-201C | 2002 ACC 2004 thr | 2002 | CCC Amino acid pro |

DNA sequence analysis of cDNA-4 corresponding to RPS2 from wild-type Col-O plants revealed an open reading frame (between two stop codons) spanning 2,751 bp. There are 2,727 bp between the first methionine codon of this reading frame and the 3'-stop codon, which corresponds to a deduced 909 amino acid polypeptide (See open reading frame "a" of FIG. 2). The amino acid sequence has a relative molecular weight of 104,460 and a pI of 6.51.

RPS2 belongs to a new class of disease resistance genes; the structure of the Rps2 polypeptide does not resemble the protein structure of the product of the only previously cloned and publicized avirulence gene-specific plant disease resistance gene, Pto, which has a putative protein kinase domain. From the above analysis of the deduced amino acid sequence, RPS2 contains several distinct protein domains conserved in other proteins from both eukaryotes and prokaryotes. These domains include but are not limited to Leucine Rich Repeats (LRR) (Kobe and Deisenhofer, (1994) Nature 366:751–756); P-loop (Saraste et al. (1990) Trends in Biological Sciences TIBS 15:430–434; Helix-Loop-Helix (Murre et al. (1989) Cell 56:777–783; and Leucine Zipper (Rodrigues and Park (1993) Mol. Cell Biol. 13:6711–6722). The amino acid sequence of Rps2 contains a LRR motif (LRR motif from amino acid residue 505 to amino acid residue 867), which is present in many known proteins and which is thought to be involved in protein-protein interactions and may thus allow interaction with other proteins that are involved in plant disease resistance. The N-terminal portion of the Rps2 polypeptide LRR is, for example, related to the LRR of yeast (*Saccharomyces cerevisiae*) adenylate cyclase, CYR1. A region predicted to be a transmembrane spanning domain (Klein et al. (1985) Biochim., Biophys. Acta 815:468–476) is located from amino acid residue 350 to amino acid residue 365, N-terminal to the LRR. An ATP/GTP binding site motif (P-loop) is predicted to be located between amino acid residue 177 and amino acid residue 194, inclusive.

From the above analysis of the deduced amino acid sequence, the Rps2 polypeptide may have a membrane-receptor structure which consists of an N-terminal extracellular region and a C-terminal cytoplasmic region. Alternatively, the topology of the Rps2 may be the opposite: an N-terminal cytoplasmic region and a C-terminal extracellular region. LRR motifs are extracellular in many cases and the Rps2 LRR contains five potential N-glycosylation sites.

Identification of RPS2 by Functional Complementation.

Complementation of rps2-201 homozygotes with genomic DNA corresponding to *Arabidopsis thaliana* functionally confirmed that the genomic region encoding cDNA-4 carries RPS2 activity. Cosmids were constructed that contained overlapping contiguous sequences of wild type *Arabidopsis thaliana* DNA from the RPS2 region contained in YACs EW11D4, EW9C3, and YUP11F1 of FIG. 1 and FIG. 4. The cosmid vectors were constructed from pSLJ4541 (obtained from J. Jones, Sainsbury Institute, Norwich, England) which contains sequences that allow the inserted sequence to be integrated into the plant genome via Agrobacterium-mediated transformation (designated "binary cosmid"). "H" and "E" cosmids (FIG. 1) were used to identify clones carrying DNA from the *Arabidopsis thaliana* genomic RPS2 region.

More than forty binary cosmids containing inserted RPS2 region DNA were used to transform rps2-201 homozygous mutants utilizing Agrobacterium-mediated transformation (Chang et al. ((1990) p. 28, Abstracts of the Fourth International Conference on Arabidopsis Research, Vienna, Austria). Transformants which remained susceptible (determined by methods including the observed absence of an HR following infection to *P. syringae* pv. *phaseolicola* strain 3121 carrying avrRpt2 and Psp 3121 without avrRpt2) indicated that the inserted DNA did not contain functional RPS2. These cosmids conferred the "Sus." or susceptible phenotype indicated in FIG. 4. Transformants which had acquired avrRpt2-specific disease resistance (determined by methods including the display of a strong hypersensitive response (HR) when inoculated with Psp 3121 with avrRpt2, but not following inoculation with Psp 3121 without avrRpt2) suggested that the inserted DNA contained a functional RPS2 gene capable of conferring the "Res." or resistant phenotype indicated in FIG. 4. Transformants obtained using the pD4 binary cosmid displayed a strong resistance phenotype as described above. The presence of the insert DNA in the transformants was confirmed by classical genetic analysis (the tight genetic linkage of the disease resistance phenotype and the kanamycin resistance phenotype conferred by the cotransformed selectable marker) and Southern analysis. These results indicated that RPS2 is encoded by a segment of the 18 kb *Arabidopsis thaliana* genomic region carried on cosmid pD4 (FIG. 4).

To further localize the RPS2 locus and confirm its ability to confer a resistance phenotype on the rps2-201 homozygous mutants, a set of six binary cosmids containing partially overlapping genomic DNA inserts were tested. The overlapping inserts pD2, pD4, pD14, pD15, pD27, and pD47 were chosen based on the location of the transcription corresponding to the five cDNA clones in the RPS2 region (FIG. 4). These transformation experiments utilized a vacuum infiltration procedure (Bechtold et al. (1993) C.R.

Acad. Sci. Paris 316:1194–1199) for Agrobacterium-mediated transformation. Agrobacterium-mediated transformations with cosmids pD2, pD14, pD15, pD39, and pD46 were performed using a root transformation/regeneration protocol (Valveekens et al. (1988), PNAS 85:5536–5540). The results of pathogen inoculation experiments assaying for RPS2 activity in these transformants is indicated in FIG. 4.

Additional transformation experiments utilized binary cosmids carrying the complete coding region and more than 1 kb of upstream genomic sequence for only cDNA-4 or cDNA-6. Using the vacuum infiltration transformation method, three independent transformants were obtained that carried the wild-type cDNA-6 genomic region in a rps2-201c homozygous background (pAD431 of FIG. 4). None of these plants displayed avrRpt2-dependent disease resistance. Homozygous rps2-201c mutants were transformed with wild-type genomic cDNA-4 (p4104 and p4115, each carrying Col-O genomic sequences corresponding to all of the cDNA-4 open reading frame, plus approximately 1.7 kb of 5' upstream sequence and approximately 0.3 kb of 3' sequence downstream of the stop codon). These p4104 and p4115 transformants displayed a disease resistance phenotype similar to the wild-type RPS2 homozygotes from which the rps2 were derived. Additional mutants (rps2-101N and rps2-101C homozygotes) also displayed avrRpt2-dependent resistance when transformed with the cDNA-4 genomic region.

RPS2 Sequences Allow Detection of Other Resistance Genes.

DNA blot analysis of *Arabidopsis thaliana* genomic DNA using RPS2 cDNA as the probe showed that Arabidopsis contains several DNA sequences that hybridize to RPS2 or a portion thereof, suggesting that there are several related genes in the Arabidopsis genome.

From the aforementioned description and the nucleic acid sequence shown in FIG. 2, it is possible to isolate other plant disease resistance genes having about 50% or greater sequence identity to the RPS2 gene. Detection and isolation can be carried out with an oligonucleotide probe containing the RPS2 gene or a portion thereof greater than about 18 nucleic acids in length. Probes to sequences encoding specific structural features of the Rps2 polypeptide are preferred as they provide a means of isolating disease resistance genes having similar structural domains. Hybridization can be done using standard techniques such as are described in Ausubel et al., *Current Protocols in Molecular Biology*, John Wiley & Sons, (1989).

For example, high stringency conditions for detecting the RPS2 gene include hybridization at about 42° C., and about 50% formamide; a first wash at about 65° C., about 2× SSC, and 1% SDS; followed by a second wash at about 65° C. and about 0.1% SSC. Lower stringency conditions for detecting RPS genes having about 50% sequence identity to the RPS2 gene are detected by, for example, hybridization at about 42° C. in the absence of formamide; a first wash at about 42° C., about 6× SSC, and about 1% SDS; and a second wash at about 50° C., about 6× SSC, and about 1% SDS. An approximately 350 nucleotide DNA probe encoding the middle portion of the LRR region of Rps2 was used as a probe in the above example. Under lower stringency conditions, a minimum of 5 DNA bands were detected in BamHI digested *Arabidopsis thaliana* genomic DNA as sequences having sufficient sequence identity to hybridize to DNA encoding the middle portion of the LRR motif of Rps2. Similar results were obtained using a probe containing a 300 nucleotide portion of the RPS2 gene encoding the extreme N-terminus of Rps2 outside of the LRR motif.

Isolation of other disease resistance genes is performed by PCR amplification techniques well known to those skilled in the art of molecular biology using oligonucleotide primers designed to amplify only sequences flanked by the oligonucleotides in genes having sequence identity to RPS2. The primers are optionally designed to allow cloning of the amplified product into a suitable vector.

RPS2 Expression in Transgenic Plant Cells and Plants

The expression of the RPS2 gene in plants susceptible to pathogens carrying avrRpt2 is achieved by introducing into a plant a DNA sequence containing the RPS2 gene for expression of the Rps2 polypeptide. A number of vectors suitable for stable transfection of plant cells or for the establishment of transgenic plants are available to the public; such vectors are described in, e.g., Pouwels et al., *Cloning Vectors: A Laboratory Manual*, 1985, Supp. 1987); Weissbach and Weissbach, *Methods for Plant Molecular Biology*, Academic Press, 1989; and Gelvin et al., *Plant Molecular Biology Manual*, Kluwer Academic Publishers, 1990. Typically, plant expression vectors include (1) one or more cloned plant genes under the transcriptional control of 5' and 3' regulatory sequences and (2) a dominant selectable marker. Such plant expression vectors may also contain, if desired, a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

An example of a useful plant promoter which could be used to express a plant resistance gene according to the invention is a caulimovirus promoter, e.g., the cauliflower mosaic virus (CaMV) 35S promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, e.g., Odel et al., Nature 313:810, (1985)). The CaMV promoter is also highly active in monocots (see, e.g., Dekeyser et al., Plant Cell 2:591, (1990); Terada and Shimamoto, Mol. Gen. Genet. 220:389, (1990)).

Other useful plant promoters include, without limitation, the nopaline synthase promoter (An et al., Plant Physiol. 88:547, (1988)) and the octopine synthase promoter (From et al., Plant Cell 1:977, (1989)).

For certain applications, it may be desirable to produce the RPS2 gene product or the avrRpt2 gene product in an appropriate tissue, at an appropriate level, or at an appropriate developmental time. Thus, there are a variety of gene promoters, each with its own distinct characteristics embodied in its regulatory sequences, shown to be regulated in response to the environment, hormones, and/or developmental cues. These include gene promoters that are responsible for (1) heat-regulated gene expression (see, e.g., Callis et al., Plant Physiol. 88: 965, (1988)), (2) light-regulated gene expression (e.g., the pea rbcS-3A described by Kuhlemeier et al., Plant Cell 1: 471, (1989); the maize rbcs promoter described by Schaffner and Sheen, Plant Cell 3: 997, (1991); or the cholorphyll a/b-binding protein gene found in pea described by Simpson et al., EMBO J. 4: 2723, (1985)), (3) hormone-regulated gene expression (e.g., the abscisic acid responsive sequences from the Em gene of wheat described Marcotte et al., Plant Cell 1:969, (1989)), (4) wound-induced gene expression (e.g., of wunI described by Siebertz et al., Plant Cell 1: 961, (1989)), or (5) organ-specific gene expression (e.g., of the tuber-specific storage protein gene described by Roshal et al., EMBO J. 6:1155, (1987); the 23-kDa zein gene from maize described by Schernthaner et al., EMBO J. 7: 1249, (1988); or the French bean β-phaseolin gene described by Bustos et al., Plant Cell 1:839, (1989)).

Plant expression vectors may also optionally include RNA processing signals, e.g, introns, which have been shown to be important for efficient RNA synthesis and accumulation (Callis et al., Genes and Dev. 1: 1183, (1987)). The location of the RNA splice sequences can influence the level of transgene expression in plants. In view of this fact, an intron may be positioned upstream or downstream of an Rps2 polypeptide-encoding sequence in the transgene to modulate levels of gene expression.

In addition to the aforementioned 5' regulatory control sequences, the expression vectors may also include regulatory control regions which are generally present in the 3' regions of plant genes (Thornburg et al., Proc. Natl Acad. Sci USA 84: 744, (1987); An et al., Plant Cell 1: 115, (1989)). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify the cells that have become transformed. Useful selectable marker genes for plant systems include genes encoding antibiotic resistance genes, for example, those encoding resistance to hygromycin, kanamycin, bleomycin, G418, streptomycin or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase, which confers resistance to the broad spectrum herbicide Basta® (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75–100 μg/ml (kanamycin), 20–50 μg/ml (hygromycin), or 5–10 μg/ml (bleomycin). A useful strategy for selection of transformants for herbicide resistance is described, e.g., in Vasil I.K., *Cell Culture and Somatic Cell Genetics of Plants*, Vol I, II, III Laboratory Procedures and Their Applications Academic Press, New York, 1984.

It should be readily apparent to one skilled in the field of plant molecular biology that the level of gene expression is dependent not only on the combination of promoters, RNA processing signals and terminator elements, but also on how these elements are used to increase the levels of gene expressions Plant Transformation Upon construction of the plant expression vector, several standard methods are known for introduction of the recombinant genetic material into the host plant for the generation of a transgenic plant. These methods include (1) Agrobacterium-mediated transformation (*A. tumefaciens* or *A. rhizogenes*) (see, e.g., Lichtenstein and Fuller In: *Genetic Engineering*, vol 6, PWJ Rigby, ed, London, Academic Press, 1987; and Lichtenstein, C. P., and Draper, J,. In: DNA Cloning, Vol II, D. M. Glover, ed, Oxford, IRI Press, 1985), (2) the particle delivery system (see, e.g., Gordon-Kamm et al., Plant Cell 2:603, (1990); or BioRad Technical Bulletin 1687, supra), (3) microinjection protocols (see, e.g., Green et al., *Plant Tissue and Cell Culture*, Academic Press, New York, 1987), (4) polyethylene glycol (PEG) procedures (see, e.g., Draper et al., Plant Cell Physiol 23:451, (1982); or e.g., Zhang and Wu, Theor. Appl. Genet. 76:835, (1988)), (5) liposome-mediated DNA uptake (see, e.g., Freeman et al., Plant Cell Physiol 25: 1353, (1984)), (6) electroporation protocols (see, e.g., Gelvin et al supra; Dekeyser et al. supra; or Fromm et al Nature 319: 791, (1986)), and (7) the vortexing method (see, e.g., Kindle, K., Proc. Natl. Acad. Sci., USA 87:1228, (1990)).

The following is an example outlining an Agrobacterium-mediated plant transformation. The general process for manipulating genes to be transferred into the genome of plant cells is carried out in two phases. First, all the cloning and DNA modification steps are done in *E. coli*, and the plasmid containing the gene construct of interest is transferred by conjugation into Agrobacterium. Second, the resulting Agrobacterium strain is used to transform plant cells. Thus, for the generalized plant expression vector, the plasmid contains an origin of replication that allows it to replicate in Agrobacterium and a high copy number origin of replication functional in *E. coli*. This permits facile production and testing of transgenes in *E. coli* prior to transfer to Agrobacterium for subsequent introduction into plants. Resistance genes can be carried on the vector, one for selection in bacteria, e.g., streptomycin, and the other that will express in plants, e.g., a gene encoding for kanamycin resistance or an herbicide resistance gene. Also present are restriction endonuclease sites for the addition of one or more transgenes operably linked to appropriate regulatory sequences and directional T-DNA border sequences which, when recognized by the transfer functions of Agrobacterium, delimit the region that will be transferred to the plant.

In another example, plant cells may be transformed by shooting into the cell tungsten microprojectiles on which cloned DNA is precipitated. In the Biolistic Apparatus (Bio-Rad, Hercules, Calif.) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to go through. As a result, the plastic macroprojectile smashes against the stopping plate and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

Transfer and expression of transgenes in plant cells is now routine practice to those skilled in the art. It has become a major tool to carry out gene expression studies and to attempt to obtain improved plant varieties of agricultural or commercial interest.

Transgenic Plant Regeneration

Plant cells transformed with a plant expression vector can be regenerated, e.g., from single cells, callus tissue or leaf discs according to standard plant tissue culture techniques. It is well known in the art that various cells, tissues and organs from almost any plant can be successfully cultured to regenerate an entire plant; such techniques are described, e.g., in Vasil supra; Green et al., supra; Weissbach and Weissbach, supra; and Gelvin et al., supra.

In one possible example, a vector carrying a selectable marker gene (e.g., kanamycin resistance), a cloned RPS2 gene under the control of its own promoter and terminator or, if desired, under the control of exogenous regulatory sequences such as the 35S CaMV promoter and the nopaline synthase terminator is transformed into Agrobacterium. Transformation of leaf tissue with vector-containing Agrobacterium is carried out as described by Horsch et al. (Science 227: 1229, (1985)). Putative transformants are selected after a few weeks (e.g., 3 to 5 weeks) on plant tissue culture media containing kanamycin (e.g. 100 µg/ml). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less media and grown in a greenhouse. Kanamycin-resistant progeny are selected by sowing surfaced sterilized seeds on hormone-free kanamycin-containing media. Analysis for the integration of the transgene is accomplished by standard techniques (see, e.g., Ausubel et al. supra; Gelvin et al. supra).

Transgenic plants expressing the selectable marker are then screened for transmission of the transgene DNA by standard immunoblot and DNA and RNA detection techniques. Each positive transgenic plant and its transgenic progeny are unique in comparison to other transgenic plants established with the same transgene. Integration of the transgene DNA into the plant genomic DNA is in most cases random and the site of integration can profoundly effect the levels, and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using Rps2 polypeptide-specific antibodies (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

Once the Rps2 polypeptide has been expressed in any cell or in a transgenic plant (e.g., as described above), it can be isolated using any standard technique, e.g., affinity chromatography. In one example, an anti-Rps2 antibody (e.g., produced as described in Ausubel et al., supra, or by any standard technique) may be attached to a column and used to isolate the polypeptide. Lysis and fractionation of Rps2-producing cells prior to affinity chromatography may be performed by standard methods (see, e.g., Ausubel et al., supra). Once isolated, the recombinant polypeptide can, if desired, be further purified, e.g., by high performance liquid chromatography (see, e.g., Fisher, Laboratory *Techniques In Biochemistry And Molecular Biology*, Work and Burdon, eds., Elsevier, 1980).

These general techniques of polypeptide expression and purification can also be used to produce and isolate useful Rps2 fragments or analogs.

Use

Introduction of RPS2 into a transformed plant cell provides for resistance to bacterial pathogens carrying the avrRpt2 avirulence gene. For example, transgenic plants of the instant invention expressing RPS2 might be used to alter, simply and inexpensively, the disease resistance of plants normally susceptible to plant pathogens carrying the avirulence gene, avrRpt2.

The invention also provides for broad-spectrum pathogen resistance by mimicking the natural mechanism of host resistance. First, the RPS2 transgene is expressed in plant cells at a sufficiently high level to initiate the plant defense response constitutively in the absence of signals from the pathogen. The level of expression associated with plant defense response initiation is determined by measuring the levels of defense response gene expression as described in Dong et al., supra. Second, the RPS2 transgene is expressed by a controllable promoter such as a tissue-specific promoter, cell-type specific promoter or by a promoter that is induced by an external signal or agent thus limiting the temporal and tissue expression of a defense response. Finally, the RPS2 gene product is co-expressed with the avrRpt2 gene product. The RPS2 gene is expressed by its natural promoter, by a constitutively expressed promoter such as the CaMV 35S promoter, by a tissue-specific or cell-type specific promoter, or by a promoter that is activated by an external signal or agent. Co-expression of RPS2 and avrRpt2 will mimic the production of gene products associated with the initiation of the plant defense response and provide resistance to pathogens in the absence of specific resistance gene-avirulence gene corresponding pairs in the host plant and pathogen.

The invention also provides for expression in plant cells of a nucleic acid having the sequence of FIG. 2 or the expression of a degenerate variant thereof encoding the amino acid sequence of open reading frame "a" of FIG. 2.

The invention further provides for the isolation of nucleic acid sequences having about 50% or greater sequence identity to RPS2 by using the RPS2 sequence of FIG. 2 or a portion thereof greater than about 18 nucleic acids in length as a probe. Appropriate reduced hybridization stringency conditions are utilized to isolate DNA sequences having about 50% or greater sequence identity to the RPS2 sequence of FIG. 2.

The invention will provide disease resistance to plants, especially crop plants, most especially important crop plants such as tomato, pepper, maize, wheat, rice and legumes such as soybean and bean, or any plant which is susceptible to pathogens carrying an avirulence gene, e.g., the avrRpt2 avirulence gene. Such pathogens include, but are not limited to, *Pseudomonas syringae* strains.

The invention also includes any biologically active fragment or analog of an Rps2 polypeptide. By "biologically active" is meant possessing any in vivo activity which is characteristic of the Rps2 polypeptide shown in FIG. 2. A useful Rps2 fragment or Rps2 analog is one which exhibits a biological activity in any biological assay for disease resistance gene product activity, for example, those assays described by Dong et al. (1991), supra; Yu et al. (1993) supra; and Kunkel et al. (1993) supra; and Whalen et al. (1991). In particular, a biologically active Rps2 polypeptide fragment or analog is capable of providing substantial resistance to plant pathogens carrying the avrRpt2 avirulence gene. By substantial resistance is meant at least partial reduction in susceptibility to plant pathogens carrying the avrRpt2 gene.

Preferred analogs include Rps2 polypeptides (or biologically active fragments thereof) whose sequences differ from the wild-type sequence (SEQ ID NOS: 2–5) only by conservative amino acid substitutions, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity.

Analogs can differ from naturally occurring Rps2 polypeptide in amino acid sequence (SEQ ID NO: 2) or can be modified in ways that do not involve sequence, or both. Analogs of the invention will generally exhibit at least 70%, preferably 80%, more preferably 90%, and most preferably 95% or even 99%, homology with a segment of 20 amino acid residues, preferably 40 amino acid residues, or more preferably the entire sequence of a naturally occurring Rps2 polypeptide sequence.

Alterations in primary sequence include genetic variants, both natural and induced. Also included are analogs that include residues other than naturally occurring L-amino acids, e.g., D-amino acids or non-naturally occurring or synthetic amino acids, e.g., β or γ amino acids. Also included in the invention are Rps2 polypeptides modified by in vivo chemical derivatization of polypeptides, including acetylation, methylation, phosphorylation, carboxylation, or glycosylation.

In addition to substantially full-length polypeptides, the invention also includes biologically active fragments of the polypeptides. As used herein, the term "fragment", as applied to a polypeptide, will ordinarily be at least 20 residues, more typically at least 40 residues, and preferably at least 60 residues in length. Fragments of Rps2 polypeptide can be generated by methods known to those skilled in the art. The ability of a candidate fragment to exhibit a biological activity of Rps2 can be assessed by those methods described herein. Also included in the invention are Rps2 polypeptides containing residues that are not required for biological activity of the peptide, e.g., those added by alternative mRNA splicing or alternative protein processing events.

Other embodiments are within the following claims.

What is claimed is:

1. A substantially pure plant DNA encoding a polypeptide comprising a P-loop and an LRR domain, said polypeptide conferring, on a plant expressing said polypeptide, resistance to a plant pathogen.

2. The DNA of claim 1, wherein said polypeptide elicits a hypersensitive response.

3. The DNA of claim 1, wherein said polypeptide is an Rps polypeptide.

4. The DNA of claim 1, wherein said DNA comprises the RPS2 gene (SEQ ID NO: 1).

5. The DNA of claim 1, wherein said DNA is genomic DNA.

6. The DNA of claim 1, wherein said DNA is cDNA.

7. The DNA of claim 1, wherein said DNA is from a plant of the genus Arabidopsis.

8. The DNA of claim 1, wherein said plant pathogen is a bacterium or a fungus.

9. The DNA of claim 1, wherein said DNA is operably linked to regulatory sequences for expression of said polypeptide, and wherein said regulatory sequences comprise a promoter.

10. The DNA of claim 9, wherein said promoter is a constitutive promoter.

11. The DNA of claim 9, wherein said promoter is inducible by one or more external agents.

12. The DNA of claim 9, wherein said promoter is cell-type specific.

13. A substantially pure plant DNA encoding the amino acid sequence of SEQ ID NO: 2 from Met$_9$ to Asn$_{885}$.

14. The DNA of claim 13, wherein said DNA is operably linked to regulatory sequences for expression of said amino acid sequence, and wherein said regulatory sequences comprise a promoter.

15. The DNA of claim 14, wherein said promoter is a constitutive promoter.

16. The DNA of claim 14, wherein said promoter is inducible by one or more external agents.

17. The DNA of claim 14, wherein said promoter is cell-type specific.

18. A substantially pure plant DNA encoding a plant resistance polypeptide having about 85% or greater sequence identity to SEQ ID NO: 1.

19. The DNA of claim 18, wherein said sequence identity is measured using the sequence analysis software package of the Genetic Computer Group.

20. The DNA of claim 18, wherein said polypeptide elicits a hypersensitive response.

21. The DNA of claim 18, wherein said DNA is operably linked to regulatory sequences for expression of said polypeptide, and wherein said regulatory sequences comprise a promoter.

22. The DNA of claim 21, wherein said promoter is a constitutive promoter.

23. The DNA of claim 21, wherein said promoter is inducible by one or more external agents.

24. The DNA of claim 21, wherein said promoter is cell-type specific.

25. A substantially pure plant DNA encoding a polypeptide comprising a P-loop and an LRR domain, said polypeptide conferring, on a plant expressing said polypeptide, resistance to a plant pathogen, wherein said P-loop and said LRR domain each comprise about 50% or greater sequence identity to a P-loop and an LRR domain of SEQ ID NO: 1.

26. The DNA of claim 25, wherein said sequence identity is measured using the sequence analysis software package of the Genetics Computer Group.

27. The DNA of claim 25, wherein said polypeptide elicits a hypersensitive response.

28. The DNA of claim 25, wherein said DNA is genomic DNA.

29. The DNA of claim 25, wherein said DNA is cDNA.

30. The DNA of claim 25, wherein said plant pathogen is a bacterium or a fungus.

31. The DNA of claim 25, wherein said DNA is operably linked to regulatory sequences for expression of said polypeptide, and wherein said regulatory sequences comprise a promoter.

32. The DNA of claim 31, wherein said promoter is a constitutive promoter.

33. The DNA of claim 31, wherein said promoter is inducible by one or more external agents.

34. The DNA of claim 31, wherein said promoter is cell-type specific.

35. A substantially pure plant DNA having about 50% or greater sequence identity to SEQ ID NO: 1, said DNA encoding a polypeptide comprising a P-loop and an LRR domain, said polypeptide conferring, on a plant expressing said polypeptide, resistance to a plant pathogen.

36. The DNA of claim 35, wherein said sequence identity is measured using the sequence analysis software package of the Genetics Computer Group.

37. The DNA of claim 35, wherein said polypeptide elicits a hypersensitive response.

38. The DNA of claim 35, wherein said DNA is genomic DNA.

39. The DNA of claim 35, wherein said DNA is cDNA.

40. The DNA of claim 35, wherein said plant pathogen is a bacterium or a fungus.

41. The DNA of claim 35, wherein said DNA is operably linked to regulatory sequences for expression of said polypeptide, and wherein said regulatory sequences comprise a promoter.

42. The DNA of claim 41, wherein said promoter is a constitutive promoter.

43. The DNA of claim 41, wherein said promoter is inducible by one or more external agents.

44. The DNA of claim 41, wherein said promoter is cell-type specific.

45. A vector comprising plant DNA encoding a polypeptide comprising a P-loop and an LRR domain, said polypeptide conferring, on a plant expressing said polypeptide, resistance to a plant pathogen, said vector directing expression of the polypeptide encoded by said DNA in a vector-containing cell.

46. A vector comprising plant DNA encoding a polypeptide having the amino acid sequence of SEQ ID NO: 2 from $Met_9$ to $Asn_{885}$, said vector directing expression of the polypeptide encoded by said DNA in a vector-containing cell.

47. A vector comprising plant DNA encoding a plant resistance polypeptide having about 85% or greater sequence identity to SEQ ID NO: 1, said vector directing expression of the polypeptide encoded by said DNA in a vector-containing cell.

48. A vector comprising plant DNA encoding a polypeptide comprising a P-loop and an LRR domain, said polypeptide conferring, on a plant expressing said polypeptide, resistance to a plant pathogen, wherein said P-loop and said LRR domain each comprise about 50% or greater sequence identity to a P-loop and an LRR domain of SEQ ID NO: 1, said vector directing expression of the polypeptide encoded by said DNA in a vector-containing cell.

49. A vector comprising plant DNA having about 50% or greater sequence identity to SEQ ID NO: 1, said DNA encoding a polypeptide comprising a P-loop and an LRR domain, said polypeptide conferring, on a plant expressing said polypeptide, resistance to a plant pathogen, said vector directing expression of the polypeptide encoded by said DNA in a vector-containing cell.

50. A vector comprising DNA of the avrRpt2 gene (SEQ ID NO: 105) operably linked to plant regulatory sequences, wherein said plant regulatory sequences comprise a promoter.

51. A vector comprising (i) plant DNA encoding a polypeptide comprising a P-loop and an LRR domain, said polypeptide conferring, on a plant expressing said potypeptide, resistance to a plant pathogen and (ii) DNA of the avrRpt2 gene (SEQ ID NO: 105), each of said DNAs operably linked to regulatory sequences which comprise a promoter.

52. A transformed bacterial cell comprising plant DNA encoding a polypeptide comprising a P-loop and an LRR domain, said polypeptide conferring, on a plant expressing said polypeptide, resistance to a plant pathogen.

53. A transformed bacterial cell comprising plant DNA encoding the amino acid sequence of SEQ ID NO: 2 from $Met_9$ to $Asn_{885}$.

54. A transformed bacterial cell comprising plant DNA encoding a plant resistance polypeptide having about 85% or greater sequence identity to SEQ ID NO: 1.

55. A transformed bacterial cell comprising plant DNA encoding a polypeptide comprising a P-loop and an LRR domain, said polypeptide conferring, on a plant expressing said polypeptide, resistance to a plant pathogen, wherein said P-loop and said LRR domain each comprise about 50% or greater sequence identity to a P-loop and an LRR domain of SEQ ID NO: 1.

56. A transformed bacterial cell comprising plant DNA having about 50% or greater sequence identity to SEQ ID NO: 1, said DNA encoding a polypeptide comprising a P-loop and an LRR domain, said polypeptide conferring, on a plant expressing said polypeptide, resistance to a plant pathogen.

57. A transformed plant cell comprising plant DNA encoding a polypeptide comprising a P-loop and an LRR domain, said polypeptide conferring, on a plant expressing said polypeptide, resistance to a plant pathogen.

58. A transformed plant cell comprising plant DNA encoding the amino acid sequence of SEQ ID NO: 2 from $Met_9$ to $Asn_{885}$.

59. A transformed plant cell comprising plant DNA encoding a plant resistance polypeptide having about 85% or greater sequence identity to SEQ ID NO: 1.

60. A transformed plant cell comprising plant DNA encoding a polypeptide comprising a P-loop and an LRR domain, said polypeptide conferring, on a plant expressing said polypeptide, resistance to a plant pathogen, wherein said P-loop and said LRR domain each comprise about 50% or greater sequence identity to a P-loop and an LRR domain of SEQ ID NO: 1.

61. A transformed plant cell comprising plant DNA having about 50% or greater sequence identity to SEQ ID NO: 1, said DNA encoding a polypeptide comprising a P-loop and an LRR domain, said polypeptide conferring, on a plant expressing said polypeptide, resistance to a plant pathogen.

62. A transformed plant cell of any one of claims 57–61, said plant cell being resistant to disease caused by a plant pathogen carrying an avirulence gene generating a signal recognized by an Rps polypeptide.

63. The transformed plant cell of claim 62, said plant pathogen carrying an avrRpt2 gene.

64. The transformed plant cell of claim 62, said plant pathogen being *Pseudomonas syringae*.

65. A transformed plant cell of any one of claims 57–61, said plant cell being selected from the group of plants consisting of Arabidopsis, tomato, soybean, bean, maize, wheat, and rice.

66. A transformed plant cell of any one of claims 57–61, wherein said DNA is operably linked to regulatory sequences, and wherein said regulatory sequences comprise a promoter.

67. The transformed plant cell of claim 66, wherein said promoter is a constitutive promoter.

68. The transformed plant cell of claim 66, wherein said promoter is inducible by one or more external agents.

69. The transformed plant cell of claim 66, wherein said promoter is cell-type specific.

70. A transgenic plant regenerated from the transformed plant cell of any one of claims 57–61.

71. A trangenic plant regenerated from a plant cell expressing (i) plant DNA encoding a polypeptide comprising a P-loop and an LRR domain, said polypeptide conferring, on a plant expressing said polypeptide, resistance to a plant pathogen and (ii) DNA of the avrRpt2 gene (SEQ ID NO: 105).

72. A transgenic plant comprising plant DNA encoding a polypeptide comprising a P-loop and an LRR domain, said polypeptide conferring, on a plant expressing said polypeptide, resistance to a plant pathogen.

73. A transgenic plant comprising plant DNA encoding the amino acid sequence of SEQ ID NO: 2 from $Met_9$ to $Asn_{885}$, wherein said DNA is expressed in said transgenic plant.

74. A transgenic plant comprising plant DNA encoding a plant resistance polypeptide having about 85% or greater sequence identity to SEQ ID NO: 1, wherein said DNA is expressed in said transgenic plant.

75. A transgenic plant comprising plant DNA encoding a polypeptide comprising a P-loop and an LRR domain, said polypeptide conferring, on a plant expressing said polypeptide, resistance to a plant pathogen, wherein said P-loop and said LRR domain each comprise about 50% or greater sequence identity to a P-loop and an LRR domain of SEQ ID NO: 1, wherein said DNA is expressed in said transgenic plant.

76. A transgenic plant comprising plant DNA having about 50% or greater sequence identity to SEQ ID NO: 1, said DNA encoding a polypeptide comprising a P-loop and an LRR domain, said polypeptide conferring, on a plant expressing said polypeptide, resistance to a plant pathogen, wherein said DNA is expressed in said transgenic plant.

77. A transgenic plant of any one of claims 71–76, wherein said DNA encodes a polypeptide or amino acid sequence that elicits a hypersensitive response.

78. A transgenic plant of any one of claims 71–76, wherein said transgenic plant is selected from the group of plants consisting of Arabidopsis, tomato, soybean, bean, maize, wheat, and rice.

79. A transgenic plant of any one of claims 71–76, wherein said DNA is operably linked to regulatory sequences for expression of said polypeptide, and wherein said regulatory sequences comprise a promoter.

80. The transgenic plant of claim 79, wherein said promoter is a constitutive promoter.

81. The transgenic plant of claim 79, wherein said promoter is inducible by one or more external agents.

82. The transgenic plant of claim 79, wherein said promoter is cell-type specific.

83. A transgenic seed from the transgenic plant of any one of claims 71–76.

84. A transformed cell from the transgenic plant of any one of claims 71–76.

85. A method of enhancing resistance to a plant pathogen in a plant, said method comprising:
(a) providing a transgenic plant cell that expresses plant DNA encoding a polypeptide comprising a P-loop and an LRR domain; and
(b) regenerating a transgenic plant from said plant cell wherein said DNA is expressed in said transgenic plant, and wherein said transgenic plant has enhanced resistance to a plant pathogen compared to a corresponding untransformed plant.

86. The method of claim 82, wherein said polypeptide elicits a hypersensitive response.

87. The method of claim 85, wherein said plant pathogen is a bacterial or a fungal pathogen.

88. The method of claim 85 said plant being selected from the group of plants consisting of Arabidopsis, tomato, soybean, bean, maize, wheat, and rice.

89. A method of enhancing resistance to a plant pathogen in a plant, said method comprising:
(a) providing a transgenic plant cell that expresses plant DNA encoding the amino acid sequence of SEQ ID NO: 2 from $Met_9$ to $Asn_{885}$; and
(b) regenerating a transgenic plant from said plant cell wherein said DNA is expressed in said transgenic plant, and wherein said transgenic plant has enhanced resistance to a plant pathogen compared to a corresponding untransformed plant.

90. The method of claim 89, wherein said polypeptide elicits a hypersensitive response.

91. The method of claim 89, wherein said plant pathogen is a bacterial or a fungal pathogen.

92. The method of claim 89, said plant being selected from the group of plants consisting of Arabidopsis, tomato, soybean, bean, maize, wheat, and rice.

93. A method of enhancing resistance to a plant pathogen in a plant, said method comprising:
(a) providing a transgenic plant cell that expresses plant DNA encoding a plant resistance polypeptide having about 85% or greater sequence identity to SEQ ID NO: 1; and
(b) regenerating a transgenic plant from said plant cell wherein said DNA is expressed in said transgenic plant, and wherein said transgenic plant has enhanced resistance to a plant pathogen compared to a corresponding untransformed plant.

94. The method of claim 93, wherein said polypeptide elicits a hypersensitive response.

95. The method of claim 93, wherein said plant pathogen is a bacterial or a fungal pathogen.

96. The method of claim 93, said plant being selected from the group of plants consisting of Arabidopsis, tomato, soybean, bean, maize, wheat, and rice.

97. A method of enhancing resistance to a plant pathogen in a plant, said method comprising:
(a) providing a transgenic plant cell that expresses plant DNA encoding a polypeptide comprising a P-loop and an LRR domain, wherein said P-loop and said LRR domain each comprise about 50% or greater sequence identity to a P-loop and an LRR domain of SEQ ID NO: 1; and
(b) regenerating a transgenic plant from said plant cell wherein said DNA is expressed in said transgenic plant, and wherein said transgenic plant has enhanced resistance to a plant pathogen compared to a corresponding untransformed plant.

98. The method of claim 97, wherein said polypeptide elicits a hypersensitive response.

99. The method of claim 97, wherein said plant pathogen is a bacterial or a fungal pathogen.

100. The method of claim 97, said plant being selected from the group of plants consisting of Arabidopsis, tomato, soybean, bean, maize, wheat, and rice.

101. A method of enhancing resistance to a plant pathogen in a plant, said method comprising:

(a) providing a transgenic plant cell that expresses plant DNA having about 50% or greater sequence identity to SEQ ID NO: 1, said DNA encoding a polypeptide comprising a P-loop and an LRR domain; and (b) regenerating a transgenic plant from said plant cell wherein said DNA is expressed in said transgenic plant, and wherein said transgenic plant has enhanced resistance to a plant pathogen compared to a corresponding untransformed plant.

102. The method of claim 101, wherein said polypeptide elicits a hypersensitive response.

103. The method of claim 101, wherein said plant pathogen is a bacterial or a fungal pathogen.

104. The method of claim 101, said plant being selected from the group of plants consisting of Arabidopsis, tomato, soybean, bean, maize, wheat, and rice.

105. A method of enhancing resistance to a plant pathogen in a plant, said method comprising:

(a) providing a transgenic plant cell that expresses (i) plant DNA encoding a polypeptide comprising a P-loop and an LRR domain, said polypeptide conferring on a plant expressing said polypeptide, resistance to a plant pathogen, and (ii) DNA of the avrRpt2 gene (SEQ ID NO: 105); and (b) regenerating a transgenic plant from said plant cell wherein each of said DNAs are expressed in said transgenic plant, and wherein said transgenic plant has enhanced resistance to a plant pathogen compared to a corresponding untransformed plant.

106. The method of claim 105, wherein said polypeptide elicits a hypersensitive response.

107. The method of claim 105, wherein said plant pathogen is a bacterial or a fungal pathogen.

108. The method of claim 105, said plant being selected from the group of plants consisting of Arabidopsis, tomato, soybean, bean, maize, wheat, and rice.

109. A method of producing a polypeptide comprising a P-loop and an LRR domain and which confers, on a plant expressing said polypeptide, resistance to a plant pathogen, said method comprising:

(a) providing a cell transformed with plant DNA encoding a polypeptide comprising a P-loop and an LRR domain, said polypeptide conferring, on a plant expressing said polypeptide, resistance to a plant pathogen;

(b) culturing said transformed cell to allow expression of said DNA; and (c) isolating said polypeptide.

110. A method of producing a polypeptide comprising a P-loop and an LRR domain and which confers, on a plant expressing said polypeptide, resistance to a plant pathogen, said method comprising:

(a) providing a cell transformed with plant DNA encoding the amino acid sequence of SEQ ID NO: 2 from $Met_9$ to $Asn_{885}$;

(b) culturing said transformed cell to allow expression of said DNA; and (c) isolating said polypeptide.

111. A method of producing a polypeptide comprising a P-loop and an LRR domain and which confers, on a plant expressing said polypeptide, resistance to a plant pathogen, said method comprising:

(a) providing a cell transformed with plant DNA encoding a plant resistance polypeptide having about 85% or greater sequence identity to SEQ ID NO: 1;

(b) culturing said transformed cell to allow expression of said DNA; and (c) isolating said polypeptide.

112. A method of producing a polypeptide comprising a P-loop and an LRR domain and which confers, on a plant expressing said polypeptide, resistance to a plant pathogen, said method comprising:

(a) providing a cell transformed with DNA encoding a polypeptide comprising a P-loop and an LRR domain, said polypeptide conferring, on a plant expressing said polypeptide, resistance to a plant pathogen, wherein said P-loop and said LRR domain each comprise about 50% or greater sequence identity to a P-loop and an LRR domain of SEQ ID NO: 1;

(b) culturing said transformed cell to allow expression of said DNA; and (c) isolating said polypeptide.

113. A method of producing a polypeptide comprising a P-loop and an LRR domain and which confers, on a plant expressing said polypeptide, resistance to a plant pathogen, said method comprising:

(a) providing a cell transformed with DNA having about 50% or greater sequence identity to SEQ ID NO: 1, said DNA encoding a polypeptide comprising a P-loop and an LRR domain, said polypeptide conferring, on a plant expressing said polypeptide, resistance to a plant pathogen;

(b) culturing said transformed cell to allow expression of said DNA; and (c) isolating said polypeptide.

* * * * *

UNITED STATES PATENT AND TRADEMARK OFFICE
CERTIFICATE OF CORRECTION

PATENT NO. : 6,127,607
DATED : October 3, 2000
INVENTOR(S) : Ausubel et al.

It is certified that error appears in the above-identified patent and that said Letters Patent is hereby corrected as shown below:

Column 78,
Line 4, "potypeptide" should be -- polypeptide --.
Line 60, "claims 57-61" should be -- claims 57-62 --.

Column 80,
Line 86, "claim 82" should be -- claim 85 --.

Signed and Sealed this

First Day of February, 2005

JON W. DUDAS
*Director of the United States Patent and Trademark Office*

SEQUENCE LISTING (1) GENERAL INFORMATION:

(iii) NUMBER OF SEQUENCES: 106

(2) INFORMATION FOR SEQ ID NO:1:

(i) SEQUENCE CHARACTERISTICS:
      (A) LENGTH: 2903 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
AAGTAAAAGA AAGAGCGAGA AATCATCGAA ATGGATTTCA TCTCATCTCT TATCGTTGGC     60

TGTGCTCAGG TGTTGTGTGA ATCTATGAAT ATGGCGGAGA GAAGAGGACA TAAGACTGAT    120

CTTAGACAAG CCATCACTGA TCTTGAAACA GCCATCGGTG ACTTGAAGGC CATACGTGAT    180

GACCTGACTT TACGGATCCA ACAAGACGGT CTAGAGGGAC GAAGCTGCTC AAATCGTGCC    240

AGAGAGTGGC TTAGTGCGGT GCAAGTAACG GAGACTAAAA CAGCCCTACT TTTAGTGAGG    300

TTTAGGCGTC GGGAACAGAG GACGCGAATG AGGAGGAGAT ACCTCAGTTG TTTCGGTTGT    360

GCCGACTACA AACTGTGCAA GAAGGTTTCT GCCATATTGA AGAGCATTGG TGAGCTGAGA    420

GAACGCTCTG AAGCTATCAA AACAGATGGC GGGTCAATTC AAGTAACTTG TAGAGAGATA    480

CCCATCAAGT CCGTTGTCGG AAATACCACG ATGATGGAAC AGGTTTTGGA ATTTCTCAGT    540

GAAGAAGAAG AAAGAGGAAT CATTGGTGTT TATGGACCTG GTGGGGTTGG GAAGACAACG    600

TTAATGCAGA GCATTAACAA CGAGCTGATC ACAAAAGGAC ATCAGTATGA TGTACTGATT    660

TGGGTTCAAA TGTCCAGAGA ATTCGGCGAG TGTACAATTC AGCAAGCCGT TGGAGCACGG    720

TTGGGTTTAT CTTGGGACGA GAAGGAGACC GGCGAAAACA GAGCTTTGAA GATATACAGA    780

GCTTTGAGAC AGAAACGTTT CTTGTTGTTG CTAGATGATG TCTGGGAAGA GATAGACTTG    840

GAGAAAACTG GAGTTCCTCG ACCTGACAGG GAAAACAAAT GCAAGGTGAT GTTCACGACA    900

CGGTCTATAG CATTATGCAA CAATATGGGT GCGGAATACA AGTTGAGAGT GGAGTTTCTG    960

GAGAAGAAAC ACGCGTGGGA GCTGTTCTGT AGTAAGGTAT GGAGAAAAGA TCTTTTAGAG   1020
```

-continued

```
TCATCATCAA TTCGCCGGCT CGCGGAGATT ATAGTGAGTA AATGTGGAGG ATTGCCACTA    1080

GCGTTGATCA CTTTAGGAGG AGCCATGGCT CATAGAGAGA CAGAAGAAGA GTGGATCCAT    1140

GCTAGTGAAG TTCTGACTAG ATTTCCAGCA GAGATGAAGG GTATGAACTA TGTATTTGCC    1200

CTTTTGAAAT TCAGCTACGA CAACCTCGAG AGTGATCTGC TTCGGTCTTG TTTCTTGTAC    1260

TGCGCTTTAT TCCCAGAAGA ACATTCTATA GAGATCGAGC AGCTTGTTGA GTACTGGGTC    1320

GGCGAAGGGT TTCTCACCAG CTCCCATGGC GTTAACACCA TTTACAAGGG ATATTTTCTC    1380

ATTGGGGATC TGAAAGCGGC ATGTTTGTTG GAAACCGGAG ATGAGAAAAC ACAGGTGAAG    1440

ATGCATAATG TGGTCAGAAG CTTTGCATTG TGGATGGCAT CTGAACAGGG GACTTATAAG    1500

GAGCTGATCC TAGTTGAGCC TAGCATGGGA CATACTGAAG CTCCTAAAGC AGAAAACTGG    1560

CGACAAGCGT TGGTGATCTC ATTGTTAGAT AACAGAATCC AGACCTTGCC TGAAAAACTC    1620

ATATGCCCGA AACTGACAAC ACTGATGCTC AACAGAACA GCTCTTTGAA GAAGATTCCA     1680

ACAGGGTTTT TCATGCATAT GCCTGTTCTC AGAGTCTTGG ACTTGTCGTT CACAAGTATC    1740

ACTGAGATTC CGTTGTCTAT CAAGTATTTG GTGGAGTTGT ATCATCTGTC TATGTCAGGA    1800

ACAAAGATAA GTGTATTGCC ACAGGAGCTT GGGAATCTTA GAAAACTGAA GCATCTGGAC    1860

CTACAAAGAA CTCAGTTTCT TCAGACGATC CCACGAGATG CCATATGTTG GCTGAGCAAG    1920

CTCGAGGTTC TGAACTTGTA CTACAGTTAC GCCGGTTGGG AACTGCAGAG CTTTGGAGAA    1980

GATGAAGCAG AAGAACTCGG ATTCGCTGAC TTGGAATACT TGGAAAACCT AACCACACTC    2040

GGTATCACTG TTCTCTCATT GGAGACCCTA AAAACTCTCT TCGAGTTCGG TGCTTTGCAT    2100

AAACATATAC AGCATCTCCA CGTTGAAGAG TGCAATGAAC TCCTCTACTT CAATCTCCCA    2160

TCACTCACTA ACCATGGCAG GAACCTGAGA AGACTTAGCA TTAAAAGTTG CCATGACTTG    2220

GAGTACCTGG TCACACCCGC AGATTTTGAA AATGATTGGC TTCCGAGTCT AGAGGTTCTG    2280

ACGTTACACA GCCTTCACAA CTTAACCAGA GTGTGGGAA ATTCTGTAAG CCAAGATTGT     2340

CTGCGGAATA TCCGTTGCAT AAACATTTCA CACTGCAACA AGCTGAAGAA TGTCTCATGG    2400

GTTCAGAAAC TCCCAAAGCT AGAGGTGATT GAACTGTTCG ACTGCAGAGA GATAGAGGAA    2460

TTGATAAGCG AACACGAGAG TCCATCCGTC GAAGATCCAA CATTGTTCCC AAGCCTGAAG    2520

ACCTTGAGAA CTAGGGATCT GCCAGAACTA AACAGCATCC TCCCATCTCG ATTTTCATTC    2580

CAAAAAGTTG AAACATTAGT CATCACAAAT TGCCCCAGAG TTAAGAAACT GCCGTTTCAG    2640

GAGAGGAGGA CCCAGATGAA CTTGCCAACA GTTTATTGTG AGGAGAAATG GTGGAAAGCA    2700

CTGGAAAAAG ATCAACCAAA CGAAGAGCTT TGTTATTTAC CGCGCTTTGT TCCAAATTGA    2760

TATAAGAGCT AAGAGCACTC TGTACAAATA TGTCCATTCA TAAGTAGCAG GAAGCCAGGA    2820

AGGTTGTTCC AGTGAAGTCA TCAACTTTCC ACATAGCCAC AAAACTAGAG ATTATGTAAT    2880

CATAAAAACC AAACTATCCG CGA                                            2903
```

(2) INFORMATION FOR SEQ ID NO:2:

(i) SEQUENCE CHARACTERISTICS:
    (A) LENGTH: 885 amino acids
    (B) TYPE: amino acid
    (C) STRANDEDNESS: Not Relevant
    (D) TOPOLOGY: linear (ii) MOLECULE TYPE: protein (xi) SEQUENCE DESCRIPTION: SEQ ID NO:2:

Lys Lys Glu Arg Glu Ile Ile Glu Met Asp Phe Ile Ser Ser Leu Ile

-continued

```
1               5                   10                  15
Val Gly Cys Ala Gln Val Leu Cys Glu Ser Met Asn Met Ala Glu Arg
                20                  25                  30
Arg Gly His Lys Thr Asp Leu Arg Gln Ala Ile Thr Asp Leu Arg Ile
            35                  40                  45
Gln Gln Asp Gly Leu Glu Gly Arg Ser Cys Ser Asn Arg Ala Arg Glu
        50                  55                  60
Trp Leu Ser Ala Val Gln Val Thr Glu Thr Lys Thr Ala Leu Leu Leu
65                  70                  75                  80
Val Arg Phe Arg Arg Glu Gln Arg Thr Arg Met Arg Arg Arg Tyr
                85                  90                  95
Leu Ser Cys Phe Gly Cys Ala Asp Tyr Lys Leu Cys Lys Lys Val Ser
                100                 105                 110
Ala Ile Leu Lys Ser Ile Gly Glu Leu Arg Glu Arg Ser Glu Ala Ile
            115                 120                 125
Lys Thr Asp Gly Gly Ser Ile Gln Val Thr Cys Arg Glu Ile Pro Ile
        130                 135                 140
Lys Ser Val Val Gly Asn Thr Thr Met Met Glu Gln Val Leu Glu Phe
145                 150                 155                 160
Leu Ser Glu Glu Glu Arg Gly Ile Ile Gly Val Tyr Gly Pro Gly
                165                 170                 175
Gly Val Gly Lys Thr Thr Leu Met Gln Ser Ile Asn Asn Glu Leu Ile
                180                 185                 190
Thr Lys Gly His Gln Tyr Asp Val Leu Ile Trp Val Gln Met Ser Arg
            195                 200                 205
Glu Phe Gly Glu Cys Thr Ile Gln Gln Ala Val Gly Ala Arg Leu Gly
        210                 215                 220
Leu Ser Trp Asp Glu Lys Glu Thr Gly Glu Asn Arg Ala Leu Lys Ile
225                 230                 235                 240
Tyr Arg Ala Leu Arg Gln Lys Arg Phe Leu Leu Leu Asp Asp Val
                245                 250                 255
Trp Glu Glu Ile Asp Leu Glu Lys Thr Gly Val Pro Arg Pro Asp Arg
                260                 265                 270
Glu Asn Lys Cys Lys Val Met Phe Thr Thr Arg Ser Ile Ala Leu Cys
            275                 280                 285
Asn Asn Met Gly Ala Glu Tyr Lys Leu Arg Val Glu Phe Leu Glu Lys
        290                 295                 300
Lys His Ala Trp Glu Leu Phe Cys Ser Lys Val Trp Arg Lys Asp Leu
305                 310                 315                 320
Leu Glu Ser Ser Ser Ile Arg Arg Leu Ala Glu Ile Ile Val Ser Lys
                325                 330                 335
Cys Gly Gly Leu Pro Leu Ala Leu Ile Thr Leu Gly Gly Ala Met Ala
                340                 345                 350
His Arg Glu Thr Glu Glu Glu Trp Ile His Ala Ser Glu Val Leu Thr
            355                 360                 365
Arg Phe Pro Ala Glu Met Lys Gly Met Asn Tyr Val Phe Ala Leu Leu
        370                 375                 380
Lys Phe Ser Tyr Asp Asn Leu Glu Ser Asp Leu Leu Arg Ser Cys Phe
385                 390                 395                 400
Leu Tyr Cys Ala Leu Phe Pro Glu Glu His Ser Ile Glu Ile Glu Gln
                405                 410                 415
Leu Val Glu Tyr Trp Val Gly Glu Gly Phe Leu Thr Ser Ser His Gly
                420                 425                 430
```

```
Val Asn Thr Ile Tyr Lys Gly Tyr Phe Leu Ile Gly Asp Leu Lys Ala
            435                 440                 445

Ala Cys Leu Leu Glu Thr Gly Asp Glu Lys Thr Gln Val Lys Met His
450                 455                 460

Asn Val Val Arg Ser Phe Ala Leu Trp Met Ala Ser Glu Gln Gly Thr
465                 470                 475                 480

Tyr Lys Glu Leu Ile Leu Val Glu Pro Ser Met Gly His Thr Glu Ala
                485                 490                 495

Pro Lys Ala Glu Asn Trp Arg Gln Ala Leu Val Ile Ser Leu Leu Asp
            500                 505                 510

Asn Arg Ile Gln Thr Leu Pro Glu Lys Leu Ile Cys Pro Lys Leu Thr
            515                 520                 525

Thr Leu Met Leu Gln Gln Asn Ser Ser Leu Lys Lys Ile Pro Thr Gly
530                 535                 540

Phe Phe Met His Met Pro Val Leu Arg Val Leu Asp Leu Ser Phe Thr
545                 550                 555                 560

Ser Ile Thr Glu Ile Pro Leu Ser Ile Lys Tyr Leu Val Glu Leu Tyr
                565                 570                 575

His Leu Ser Met Ser Gly Thr Lys Ile Ser Val Leu Pro Gln Glu Leu
            580                 585                 590

Gly Asn Leu Arg Lys Leu Lys His Leu Asp Leu Gln Arg Thr Gln Phe
            595                 600                 605

Leu Gln Thr Ile Pro Arg Asp Ala Ile Cys Trp Leu Ser Lys Leu Glu
        610                 615                 620

Val Leu Asn Leu Tyr Tyr Ser Tyr Ala Gly Trp Glu Leu Gln Ser Phe
625                 630                 635                 640

Gly Glu Asp Glu Ala Glu Leu Gly Phe Ala Asp Leu Glu Tyr Leu
                645                 650                 655

Glu Asn Leu Thr Thr Leu Gly Ile Thr Val Leu Ser Leu Glu Thr Leu
                660                 665                 670

Lys Thr Leu Phe Glu Phe Gly Ala Leu His Lys His Ile Gln His Leu
        675                 680                 685

His Val Glu Glu Cys Asn Glu Leu Leu Tyr Phe Asn Leu Pro Ser Leu
690                 695                 700

Thr Asn His Gly Arg Asn Leu Arg Arg Leu Ser Ile Lys Ser Cys His
705                 710                 715                 720

Asp Leu Glu Tyr Leu Val Thr Pro Ala Asp Phe Glu Asn Asp Trp Leu
                725                 730                 735

Pro Ser Leu Glu Val Leu Thr Leu His Ser Leu His Asn Leu Arg Cys
            740                 745                 750

Ile Asn Ile Ser His Cys Asn Lys Leu Lys Asn Val Ser Trp Val Gln
            755                 760                 765

Lys Leu Pro Lys Leu Glu Val Ile Glu Leu Phe Asp Cys Arg Glu Ile
        770                 775                 780

Glu Glu Leu Ile Ser Glu His Glu Ser Pro Ser Val Glu Asp Pro Thr
785                 790                 795                 800

Leu Phe Pro Ser Leu Lys Thr Leu Arg Thr Arg Asp Leu Pro Glu Leu
                805                 810                 815

Asn Ser Ile Leu Pro Ser Arg Phe Ser Phe Gln Lys Val Glu Thr Leu
            820                 825                 830

Val Ile Thr Asn Cys Pro Arg Val Lys Lys Leu Pro Phe Gln Glu Arg
            835                 840                 845
```

```
Arg Thr Gln Met Asn Leu Pro Thr Val Tyr Cys Glu Glu Lys Trp Trp
    850                 855                 860

Lys Ala Leu Glu Lys Asp Gln Pro Asn Glu Glu Leu Cys Tyr Leu Pro
865                 870                 875                 880

Arg Phe Val Pro Asn
                885

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:3:

Glu His Ser Val Gln Ile Cys Pro Phe Ile Ser Ser Arg Lys Pro Gly
1               5                   10                  15

Arg Leu Phe Gln
            20

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:4:

Ser His Gln Leu Ser Thr
1               5

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

Arg Leu Cys Asn His Lys Asn Gln Thr Ile Arg
1               5                   10

(2) INFORMATION FOR SEQ ID NO:6:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

Ser Lys Arg Lys Ser Glu Lys Ser Ser Lys Trp Ile Ser Ser His Leu
1               5                   10                  15

Leu Ser Leu Ala Val Leu Arg Cys Cys Val Asn Leu
            20                  25
```

(2) INFORMATION FOR SEQ ID NO:7:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:7:

```
Ile Trp Arg Arg Glu Glu Asp Ile Arg Leu Ile Leu Asp Lys Pro Ser
 1               5                  10                  15

Leu Ile Leu Lys Gln Pro Ser Val Thr
            20                  25
```

(2) INFORMATION FOR SEQ ID NO:8:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:8:

```
Arg Pro Tyr Val Met Thr
 1               5
```

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

```
Leu Tyr Gly Ser Asn Lys Thr Val
 1               5
```

(2) INFORMATION FOR SEQ ID NO:10:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:10:

```
Arg Asp Glu Ala Ala Gln Ile Val Pro Glu Ser Gly Leu Val Arg Cys
 1               5                  10                  15

Lys
```

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:11:

Arg Arg Leu Lys Gln Pro Tyr Phe
1               5

(2) INFORMATION FOR SEQ ID NO:12:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:12:

Gly Leu Gly Val Gly Asn Arg Gly Arg Glu
1               5                   10

(2) INFORMATION FOR SEQ ID NO:13:

(i) SEQUENCE CHARACTERISTICS:
            (A) LENGTH: 22 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:13:

Gly Gly Asp Thr Ser Val Val Ser Val Val Pro Thr Thr Asn Cys Ala
1               5                   10                  15

Arg Arg Phe Leu Pro Tyr
            20

(2) INFORMATION FOR SEQ ID NO:14:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:14:

Arg Ala Leu Val Ser
1               5

(2) INFORMATION FOR SEQ ID NO:15:

(i) SEQUENCE CHARACTERISTICS:
            (A) LENGTH: 15 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:15:

Glu Asn Ala Leu Lys Leu Ser Lys Gln Met Ala Gly Gln Phe Lys
1               5                   10                  15

(2) INFORMATION FOR SEQ ID NO:16:

(i) SEQUENCE CHARACTERISTICS:
            (A) LENGTH: 15 amino acids
            (B) TYPE: amino acid -continued

```
        (C) STRANDEDNESS: Not Relevant
        (D) TOPOLOGY: linear (ii) MOLECULE TYPE: protein (xi) SEQUENCE DESCRIPTION: SEQ ID NO:16:

Leu Val Glu Arg Tyr Pro Ser Ser Pro Leu Ser Glu Ile Pro Arg
1               5                  10                  15

(2) INFORMATION FOR SEQ ID NO:17:

(i) SEQUENCE CHARACTERISTICS:
        (A) LENGTH: 29 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:17:

Trp Asn Arg Phe Trp Asn Phe Ser Val Lys Lys Lys Glu Glu Ser
1               5                  10                  15

Leu Val Phe Met Asp Leu Val Gly Leu Gly Arg Gln Arg
                20                  25

(2) INFORMATION FOR SEQ ID NO:18:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:18:

Cys Arg Ala Leu Thr Thr Ser
1               5

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:19:

Ser Gln Lys Asp Ile Ser Met Met Tyr
1               5

(2) INFORMATION FOR SEQ ID NO:20:

(i) SEQUENCE CHARACTERISTICS:
        (A) LENGTH: 36 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:20:

Phe Gly Phe Lys Cys Pro Glu Asn Ser Ala Ser Val Gln Phe Ser Lys
1               5                  10                  15

Pro Leu Glu His Gly Trp Val Tyr Leu Gly Thr Arg Arg Pro Ala
                20                  25                  30
```

```
Lys Thr Glu Leu
        35

(2) INFORMATION FOR SEQ ID NO:21:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:21:

Arg Tyr Thr Glu Leu
1               5

(2) INFORMATION FOR SEQ ID NO:22:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:22:

Asp Arg Asn Val Ser Cys Cys Cys
1               5

(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:23:

Met Met Ser Gly Lys Arg
1               5

(2) INFORMATION FOR SEQ ID NO:24:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:24:

Thr Trp Arg Lys Leu Glu Phe Leu Asp Leu Thr Gly Lys Thr Asn Ala
1               5                   10                  15

Arg (2) INFORMATION FOR SEQ ID NO:25:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear
```

```
        (ii) MOLECULE TYPE: protein (xi) SEQUENCE DESCRIPTION: SEQ ID NO:25:

Cys Ser Arg His Gly Leu
1               5

(2) INFORMATION FOR SEQ ID NO:26:

(i) SEQUENCE CHARACTERISTICS:
            (A) LENGTH: 11 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:26:

His Tyr Ala Thr Ile Trp Val Arg Asn Thr Ser
1               5                   10

(2) INFORMATION FOR SEQ ID NO:27:

(i) SEQUENCE CHARACTERISTICS:
            (A) LENGTH: 23 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:27:

Glu Trp Ser Phe Trp Arg Arg Asn Thr Arg Gly Ser Cys Ser Val Val
1               5                   10                  15

Arg Tyr Gly Glu Lys Ile Phe
            20

(2) INFORMATION FOR SEQ ID NO:28:

(i) SEQUENCE CHARACTERISTICS:
            (A) LENGTH: 11 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:28:

Ser His His Gln Phe Ala Gly Ser Arg Arg Leu
1               5                   10

(2) INFORMATION FOR SEQ ID NO:29:

(i) SEQUENCE CHARACTERISTICS:
            (A) LENGTH: 7 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:29:

Val Asn Val Glu Asp Cys His
1               5

(2) INFORMATION FOR SEQ ID NO:30:

(i) SEQUENCE CHARACTERISTICS:
            (A) LENGTH: 19 amino acids
```

(B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:30:

Glu Glu Pro Trp Leu Ile Glu Arg Gln Lys Lys Ser Gly Ser Met Leu
1               5                   10                  15

Val Lys Phe (2) INFORMATION FOR SEQ ID NO:31:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:31:

Leu Asp Phe Gln Gln Arg
1               5

(2) INFORMATION FOR SEQ ID NO:32:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:32:

Thr Met Tyr Leu Pro Phe
1               5

(2) INFORMATION FOR SEQ ID NO:33:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:33:

Asn Ser Ala Thr Thr Thr Ser Arg Val Ile Cys Phe Gly Leu Val Ser
1               5                   10                  15

Cys Thr Ala Leu Tyr Ser Gln Lys Asn Ile Leu
                20                  25

(2) INFORMATION FOR SEQ ID NO:34:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:34:

Lys Arg His Val Cys Trp Lys Pro Glu Met Arg Lys His Arg
1               5                   10

(2) INFORMATION FOR SEQ ID NO:35:

(i) SEQUENCE CHARACTERISTICS:
        (A) LENGTH: 33 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:35:

```
Arg Ser Ser Ser Leu Leu Ser Thr Gly Ser Ala Lys Gly Phe Ser Pro
 1               5                  10                  15

Ala Pro Met Ala Leu Thr Pro Phe Thr Arg Asp Ile Phe Ser Leu Gly
            20                  25                  30

Ile
```

(2) INFORMATION FOR SEQ ID NO:36:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:36:

```
Arg Cys Ile Met Trp Ser Glu Ala Leu His Cys Gly Trp His Leu Asn
 1               5                  10                  15

Arg Gly Leu Ile Arg Ser
            20
```

(2) INFORMATION FOR SEQ ID NO:37:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:37:

```
Leu Ser Leu Ala Trp Asp Ile Leu Lys Leu Leu Lys Gln Lys Thr Gly
 1               5                  10                  15

Asp Lys Arg Trp
            20
```

(2) INFORMATION FOR SEQ ID NO:38:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:38:

```
Ile Thr Glu Ser Arg Pro Cys Leu Lys Asn Ser Tyr Ala Arg Asn
 1               5                  10                  15
```

(2) INFORMATION FOR SEQ ID NO:39:

-continued

```
    (i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:39:

Cys Ser Asn Arg Thr Ala Leu
1               5

(2) INFORMATION FOR SEQ ID NO:40:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:40:

Arg Arg Phe Gln Gln Gly Phe Ser Cys Ile Cys Leu Phe Ser Glu Ser
1               5                  10                  15

Trp Thr Cys Arg Ser Gln Val Ser Leu Arg Phe Arg Cys Leu Ser Ser
            20                  25                  30

Ile Trp Trp Ser Cys Ile Ile Cys Leu Cys Gln Glu Gln Arg
            35                  40                  45

(2) INFORMATION FOR SEQ ID NO:41:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:41:

Val Tyr Cys His Arg Ser Leu Gly Ile Leu Glu Asn
1               5                  10

(2) INFORMATION FOR SEQ ID NO:42:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:42:

Ser Ile Trp Thr Tyr Lys Glu Leu Ser Phe Phe Arg Arg Ser His Glu
1               5                  10                  15

Met Pro Tyr Val Gly
            20

(2) INFORMATION FOR SEQ ID NO:43:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear
```

(ii) MOLECULE TYPE: protein (xi) SEQUENCE DESCRIPTION: SEQ ID NO:43:

Ala Ser Ser Arg Phe
1               5

(2) INFORMATION FOR SEQ ID NO:44:

(i) SEQUENCE CHARACTERISTICS:
          (A) LENGTH: 32 amino acids
          (B) TYPE: amino acid
          (C) STRANDEDNESS: Not Relevant
          (D) TOPOLOGY: linear (ii) MOLECULE TYPE: protein (xi) SEQUENCE DESCRIPTION: SEQ ID NO:44:

Thr Cys Thr Thr Val Thr Pro Val Gly Asn Cys Arg Ala Leu Glu Lys
1               5                  10                  15

Met Lys Gln Lys Asn Ser Asp Ser Leu Thr Trp Asn Thr Trp Lys Thr
            20                  25                  30

(2) INFORMATION FOR SEQ ID NO:45:

(i) SEQUENCE CHARACTERISTICS:
          (A) LENGTH: 12 amino acids
          (B) TYPE: amino acid
          (C) STRANDEDNESS: Not Relevant
          (D) TOPOLOGY: linear (ii) MOLECULE TYPE: protein (xi) SEQUENCE DESCRIPTION: SEQ ID NO:45:

Pro His Ser Val Ser Leu Phe Ser His Trp Arg Pro
1               5                  10

(2) INFORMATION FOR SEQ ID NO:46:

(i) SEQUENCE CHARACTERISTICS:
          (A) LENGTH: 38 amino acids
          (B) TYPE: amino acid
          (C) STRANDEDNESS: Not Relevant
          (D) TOPOLOGY: linear (ii) MOLECULE TYPE: protein (xi) SEQUENCE DESCRIPTION: SEQ ID NO:46:

Lys Leu Ser Ser Ser Val Leu Cys Ile Asn Ile Tyr Ser Ile Ser
1               5                  10                  15

Thr Leu Lys Ser Ala Met Asn Ser Ser Thr Ser Ile Ser His His Ser
            20                  25                  30

Leu Thr Met Ala Gly Thr
        35

(2) INFORMATION FOR SEQ ID NO:47:

(i) SEQUENCE CHARACTERISTICS:
          (A) LENGTH: 27 amino acids
          (B) TYPE: amino acid
          (C) STRANDEDNESS: Not Relevant
          (D) TOPOLOGY: linear (ii) MOLECULE TYPE: protein (xi) SEQUENCE DESCRIPTION: SEQ ID NO:47:

Glu Asp Leu Ala Leu Lys Val Ala Met Thr Trp Ser Thr Trp Ser His
1               5                  10                  15

```
Pro Gln Ile Leu Lys Met Ile Gly Phe Arg Val
            20                  25
```

(2) INFORMATION FOR SEQ ID NO:48:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:48:

```
Arg Tyr Thr Ala Phe Thr Thr
1               5
```

(2) INFORMATION FOR SEQ ID NO:49:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:49:

```
Pro Glu Cys Gly Glu Ile Leu
1               5
```

(2) INFORMATION FOR SEQ ID NO:50:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:50:

```
Phe Arg Asn Ser Gln Ser
1               5
```

(2) INFORMATION FOR SEQ ID NO:51:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:51:

```
Ala Lys Ile Val Cys Gly Ile Ser Val Ala
1               5                   10
```

(2) INFORMATION FOR SEQ ID NO:52:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:52:

Thr Phe His Thr Ala Thr Ser
1               5

(2) INFORMATION FOR SEQ ID NO:53:

(i) SEQUENCE CHARACTERISTICS:
            (A) LENGTH: 8 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:53:

Leu Asn Cys Ser Thr Ala Glu Arg
1               5

(2) INFORMATION FOR SEQ ID NO:54:

(i) SEQUENCE CHARACTERISTICS:
            (A) LENGTH: 16 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:54:

Ala Asn Thr Arg Val His Pro Ser Lys Ile Gln His Cys Ser Gln Ala
1               5                   10                  15

(2) INFORMATION FOR SEQ ID NO:55:

(i) SEQUENCE CHARACTERISTICS:
            (A) LENGTH: 7 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:55:

Glu Leu Gly Ile Cys Gln Asn
1               5

(2) INFORMATION FOR SEQ ID NO:56:

(i) SEQUENCE CHARACTERISTICS:
            (A) LENGTH: 15 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:56:

Thr Ala Ser Ser His Leu Asp Phe His Ser Lys Lys Leu Lys His
1               5                   10                  15

(2) INFORMATION FOR SEQ ID NO:57:

(i) SEQUENCE CHARACTERISTICS:
            (A) LENGTH: 19 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:57:

Ser Ser Gln Ile Ala Pro Glu Leu Arg Asn Cys Arg Phe Arg Arg Gly
1               5                   10                  15

Gly Pro Arg (2) INFORMATION FOR SEQ ID NO:58:

(i) SEQUENCE CHARACTERISTICS:
        (A) LENGTH: 47 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:58:

Thr Cys Gln Gln Phe Ile Val Arg Arg Asn Gly Gly Lys His Trp Lys
1               5                   10                  15

Lys Ile Asn Gln Thr Lys Ser Phe Val Ile Tyr Arg Ala Leu Phe Gln
                20                  25                  30

Ile Asp Ile Arg Ala Lys Ser Thr Leu Tyr Lys Tyr Val His Ser
            35                  40                  45

(2) INFORMATION FOR SEQ ID NO:59:

(i) SEQUENCE CHARACTERISTICS:
        (A) LENGTH: 33 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:59:

Val Ala Gly Ser Gln Glu Gly Cys Ser Ser Glu Val Ile Asn Phe Pro
1               5                   10                  15

His Ser His Lys Thr Arg Asp Tyr Val Ile Ile Lys Thr Lys Leu Ser
                20                  25                  30

Ala (2) INFORMATION FOR SEQ ID NO:60:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:60:

Val Lys Glu Arg Ala Arg Asn His Arg Asn Gly Phe His Leu Ile Ser
1               5                   10                  15

Tyr Arg Trp Leu Cys Ser Gly Val Val
                20                  25

(2) INFORMATION FOR SEQ ID NO:61:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:61:

Ile Tyr Glu Tyr Gly Gly Glu Lys Arg Thr
1               5                   10

(2) INFORMATION FOR SEQ ID NO:62:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:62:

Leu Glu Gly His Thr
1               5

(2) INFORMATION FOR SEQ ID NO:63:

(i) SEQUENCE CHARACTERISTICS:
            (A) LENGTH: 23 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:63:

Pro Asp Phe Thr Asp Pro Thr Arg Arg Ser Arg Gly Thr Lys Leu Leu
1               5                   10                  15

Lys Ser Cys Gln Arg Val Ala
            20

(2) INFORMATION FOR SEQ ID NO:64:

(i) SEQUENCE CHARACTERISTICS:
            (A) LENGTH: 7 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:64:

Cys Gly Ala Ser Asn Gly Asp
1               5

(2) INFORMATION FOR SEQ ID NO:65:

(i) SEQUENCE CHARACTERISTICS:
            (A) LENGTH: 8 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:65:

Asn Ser Pro Thr Phe Ser Glu Val
1               5

(2) INFORMATION FOR SEQ ID NO:66:

(i) SEQUENCE CHARACTERISTICS:
            (A) LENGTH: 35 amino acids (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:66:

Ala Ser Gly Thr Glu Asp Ala Asn Glu Glu Ile Pro Gln Leu Phe
1               5                   10                  15

Arg Leu Cys Arg Leu Gln Thr Val Gln Gly Phe Cys His Ile Glu
            20                  25                  30

Glu His Trp
        35

(2) INFORMATION FOR SEQ ID NO:67:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:67:

Ala Glu Arg Thr Leu
1               5

(2) INFORMATION FOR SEQ ID NO:68:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:68:

Ser Tyr Gln Asn Arg Trp Arg Val Asn Ser Ser Asn Leu
1               5                   10

(2) INFORMATION FOR SEQ ID NO:69:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:69:

Arg Asp Thr His Gln Val Arg Cys Arg Lys Tyr His Asp Asp Gly Thr
1               5                   10                  15

Gly Phe Gly Ile Ser Gln
            20

(2) INFORMATION FOR SEQ ID NO:70:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:70:

Arg Arg Arg Lys Arg Asn His Trp Cys Leu Trp Thr Trp Trp Gly Trp
1               5                   10                  15

Glu Asp Asn Val Asn Ala Glu His
            20

(2) INFORMATION FOR SEQ ID NO:71:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:71:

Gln Arg Ala Asp His Lys Arg Thr Ser Val
1               5                   10

(2) INFORMATION FOR SEQ ID NO:72:

(i) SEQUENCE CHARACTERISTICS:
        (A) LENGTH: 55 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:72:

Cys Thr Asp Leu Gly Ser Asn Val Gln Arg Ile Arg Arg Val Tyr Asn
1               5                   10                  15

Ser Ala Ser Arg Trp Ser Thr Val Gly Phe Ile Leu Gly Arg Glu Gly
                20                  25                  30

Asp Arg Arg Lys Gln Ser Phe Glu Asp Ile Gln Ser Phe Glu Thr Glu
            35                  40                  45

Thr Phe Leu Val Val Ala Arg
    50                  55

(2) INFORMATION FOR SEQ ID NO:73:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:73:

Cys Leu Gly Arg Asp Arg Leu Gly Glu Asn Trp Ser Ser Ser Thr
1               5                   10                  15

(2) INFORMATION FOR SEQ ID NO:74:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:74:

Arg Asp Arg Arg Arg Val Asp Pro Cys

```
1               5
```

(2) INFORMATION FOR SEQ ID NO:75:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:75:

```
Gln Gly Lys Gln Met Gln Gly Asp Val His Asp Thr Val Tyr Ser Ile
1               5                  10                  15

Met Gln Gln Tyr Gly Cys Gly Ile Gln Val Glu Ser Gly Val Ser Gly
            20                  25                  30

Glu Glu Thr Arg Val Gly Ala Val Leu
        35                  40
```

(2) INFORMATION FOR SEQ ID NO:76:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:76:

```
Gly Met Glu Lys Arg Ser Phe Arg Val Ile Ile Asn Ser Pro Ala Arg
1               5                  10                  15

Gly Asp Tyr Ser Glu
            20
```

(2) INFORMATION FOR SEQ ID NO:77:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:77:

```
Met Trp Arg Ile Ala Thr Ser Val Asp His Phe Arg Arg Ser His Gly
1               5                  10                  15

Ser
```

(2) INFORMATION FOR SEQ ID NO:78:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:78:

```
Ile Ser Ser Arg Asp Glu Gly Tyr Glu Leu Cys Ile Cys Pro Phe Glu
1               5                  10                  15

Ile Gln Leu Arg Gln Pro Arg Glu
            20
```

(2) INFORMATION FOR SEQ ID NO:79:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:79:

Ser Ala Ser Val Leu Phe Leu Val Leu Arg Phe Ile Pro Arg Arg Thr
1               5                   10                  15

Phe Tyr Arg Asp Arg Ala Ala Cys
            20

(2) INFORMATION FOR SEQ ID NO:80:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:80:

Val Leu Gly Arg Arg Arg Val Ser His Gln Leu Pro Trp Arg
1               5                   10

(2) INFORMATION FOR SEQ ID NO:81:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:81:

His His Leu Gln Gly Ile Phe Ser His Trp Gly Ser Glu Ser Gly Met
1               5                   10                  15

Phe Val Gly Asn Arg Arg
            20

(2) INFORMATION FOR SEQ ID NO:82:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:82:

Glu Asn Thr Gly Glu Asp Ala
1               5

(2) INFORMATION FOR SEQ ID NO:83:

(i) SEQUENCE CHARACTERISTICS:
        (A) LENGTH: 43 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:83:

Lys Thr His Met Pro Glu Thr Asp Asn Thr Asp Ala Pro Thr Glu Gly
1               5                   10                  15

Leu Phe Glu Glu Asp Ser Asn Arg Val Phe His Ala Tyr Ala Cys Ser
                20                  25                  30

Gln Ser Leu Gly Leu Val Val His Lys Tyr His
            35                  40

(2) INFORMATION FOR SEQ ID NO:84:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:84:

Cys Gly Gln Lys Leu Cys Ile Val Asp Gly Ile
1               5                   10

(2) INFORMATION FOR SEQ ID NO:85:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:85:

Gly Ala Asp Pro Ser
1               5

(2) INFORMATION FOR SEQ ID NO:86:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:86:

Ser Arg Lys Leu Ala Thr Ser Val Gly Asp Leu Ile Val Arg
1               5                   10

(2) INFORMATION FOR SEQ ID NO:87:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:87:

Gln Asn Pro Asp Leu Ala
1               5

(2) INFORMATION FOR SEQ ID NO:88:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:88:

Asp Ser Val Val Tyr Gln Val Phe Gly Gly Val Val Ser Val Tyr
1               5                  10                  15

Val Arg Asn Lys Asp Lys Cys Ile Ala Thr Gly Ala Trp Glu Ser
            20                  25                  30

(2) INFORMATION FOR SEQ ID NO:89:

(i) SEQUENCE CHARACTERISTICS:
        (A) LENGTH: 47 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:89:

Lys Thr Glu Ala Ser Gly Pro Thr Lys Asn Ser Val Ser Ser Asp Asp
1               5                  10                  15

Pro Thr Arg Cys His Met Leu Ala Glu Gln Ala Arg Gly Ser Glu Leu
            20                  25                  30

Val Leu Gln Leu Arg Arg Leu Gly Thr Ala Glu Leu Trp Arg Arg
        35                  40                  45

(2) INFORMATION FOR SEQ ID NO:90:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:90:

Ser Arg Arg Thr Arg Ile Arg
1               5

(2) INFORMATION FOR SEQ ID NO:91:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:91:

Leu Gly Ile Leu Gly Lys Pro Asn His Thr Arg Tyr His Cys Ser Leu
1               5                  10                  15

Ile Gly Asp Pro Lys Asn Ser Leu Arg Val Arg Cys Phe Ala
            20                  25                  30

(2) INFORMATION FOR SEQ ID NO:92:

(i) SEQUENCE CHARACTERISTICS:

(A) LENGTH: 7 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:92:

Thr Tyr Thr Ala Ser Pro Arg
1               5

(2) INFORMATION FOR SEQ ID NO:93:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:93:

Thr Pro Leu Leu Gln Ser Pro Ile Thr His
1               5                   10

(2) INFORMATION FOR SEQ ID NO:94:

(i) SEQUENCE CHARACTERISTICS:
            (A) LENGTH: 8 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:94:

Pro Trp Gln Glu Pro Glu Lys Thr
1               5

(2) INFORMATION FOR SEQ ID NO:95:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:95:

Leu Gly Val Pro Gly His Thr Arg Arg Phe
1               5                   10

(2) INFORMATION FOR SEQ ID NO:96:

(i) SEQUENCE CHARACTERISTICS:
            (A) LENGTH: 58 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:96:

Leu Ala Ser Glu Ser Arg Gly Ser Asp Val Thr Gln Pro Ser Gln Leu
1               5                   10                  15

Asn Gln Ser Val Gly Lys Phe Cys Lys Pro Arg Leu Ser Ala Glu Tyr
            20                  25                  30

```
Pro Leu His Lys His Phe Thr Leu Gln Gln Ala Glu Glu Cys Leu Met
        35                  40                  45
Gly Ser Glu Thr Pro Lys Ala Arg Gly Asp
    50                  55
```

(2) INFORMATION FOR SEQ ID NO:97:

(i) SEQUENCE CHARACTERISTICS:
        (A) LENGTH: 33 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:97:

```
Thr Val Arg Leu Gln Arg Asp Arg Gly Ile Asp Lys Arg Thr Arg Glu
1               5                   10                  15
Ser Ile Arg Arg Arg Ser Asn Ile Val Pro Lys Pro Glu Asp Leu Glu
            20                  25                  30
Asn
```

(2) INFORMATION FOR SEQ ID NO:98:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:98:

```
Gly Ser Ala Arg Thr Lys Gln His Pro Pro Ile Ser Ile Phe Ile Pro
1               5                   10                  15
Lys Ser
```

(2) INFORMATION FOR SEQ ID NO:99:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:99:

```
Asn Ile Ser His His Lys Leu Pro Gln Ser
1               5                   10
```

(2) INFORMATION FOR SEQ ID NO:100:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:100:

```
Glu Thr Ala Val Ser Gly Glu Glu Asp Pro Asp Glu Leu Ala Asn Ser
1               5                   10                  15
Leu Leu
```

(2) INFORMATION FOR SEQ ID NO:101:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: protein (xi) SEQUENCE DESCRIPTION: SEQ ID NO:101:

GGTAGTGAGT AGAGAATAAC                                    20

(2) INFORMATION FOR SEQ ID NO:102:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:102:

Glu Leu Arg Ala Leu Cys Thr Asn Met Ser Ile His Lys
1             5                  10

(2) INFORMATION FOR SEQ ID NO:103:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:103:

Gln Glu Ala Arg Lys Val Val Pro Val Lys Ser Ser Thr Phe His Ile
1             5                  10              15

Ala Thr Lys Leu Glu Ile Met
          20

(2) INFORMATION FOR SEQ ID NO:104:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:104:

Lys Pro Asn Tyr Pro Arg
1             5

(2) INFORMATION FOR SEQ ID NO:105:

(i) SEQUENCE CHARACTERISTICS:
        (A) LENGTH: 1491 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:105:

-continued

```
ATCGATTGAT CTCTGGCTCA GTGCGAGTAG TCCATTTGAG AGCAGTCGTA GCCCCGCGTG    60

GCGCATCATG GAGCTATTTG GAATTTTCGC AGGGTTATCG ATTCGTAGTG GAACCCATT    120

CATTGTTTGG AACCACCAAC GGACGACTTA ACAAGCTCCC CGAGGTGCAT GATGAAAATT   180

GCTCCAGTTG CCATAAATCA CAGCCCGCTC AGCAGGGAGG TCCCGTCACA CGCGGCACCC   240

ACTCAGGCAA AGCAAACCAA CCTTCAATCT GAAGCTGGCG ATTTAGATGC AAGAAAAAGT   300

AGCGCTTCAA GCCCGGAAAC CCGCGCATTA CTCGCTACTA AGACAGTACT CGGGAGACAC   360

AAGATAGAGG TTCCGGCCTT TGGAGGGTGG TTCAAAAAGA AATCATCTAA GCACGAGACG   420

GGCGGTTCAA GTGCCAACGC AGATAGTTCG AGCGTGGCTT CCGATTCCAC CGAAAAACCT   480

TTGTTCCGTC TCACGCACGT TCCTTACGTA TCCCAAGGTA ATGAGCGAAT GGGATGTTGG   540

TATGCCTGCG CAAGAATGGT TGGCCATTCT GTCGAAGCTG GGCCTCGCCT AGGGCTGCCG   600

GAGCTCTATG AGGGAAGGGA GGCGCCAGCT GGGCTACAAG ATTTTTCAGA TGTAGAAAGG   660

TTTATTCACA ATGAAGGATT AACTCGGGTA GACCTTCCAG ACAATGAGAG ATTTACACAC   720

GAAGAGTTGG GTGCACTGTT GTATAAGCAC GGGCCGATTA TATTTGGGTG GAAAACTCCG   780

AATGACAGCT GGCACATGTC GGTCCTCACT GGTGTCGATA AGAGACGTC GTCCATTACT    840

TTTCACGATC CCCGACAGGG GCCGGACCTA GCAATGCCGC TCGATTACTT TAATCAGCGA   900

TTGGCATGGC AGGTTCCACA CGCAATGCTC TACCGCTAAG TAGCAGGGTA TCTTCACGTG   960

GCGGCATCAT GACAAGCCCA TGATGCCGCC AGCAGCTACC TGAATGCCGT CTGGCTTTTT  1020

GGTCCCTATT GTCGTATCCG GAAGATGACG TCAAAGAATC TCGGCAAGAG CTTTCTTGCT  1080

CGACTCCTCA GCTTCCGGAT CGATCAGGTC GCTTGCCAGA GCGCGCTTGT CCATGAGCAT  1140

CTGCCACAGC TGCTGGTCGA TGGTGTCCTC AGCTAAAGGG ATTTTGACGA CAACCATGCG  1200

CAACTGCCCG TTGCGATACG CTCGATCCTG AAGCCCCGGT GTCCATGGCA GCCCCAAGAA  1260

AAAGACATAG TTCGCCGCTG TGAGGTTGTA GCCTGTGCCG GCGGCCGACC TGGTCCCGAT  1320

AAACACCCTG CAGTCCGGAT CCTGCTGGAA AGCATCAATC GCCTTCTGCC GCTTCTTGGG  1380

CGAGTCACTG CCCACCAACG TCACGCACCC GACGCCAAGC TTGAGGCAGT GCTCCCGCAA  1440

CGTGGCCACG GATTCCTGAT ACTCGCAGAA GAGGATCACC TTGTCGTCGA C           1491
```

(2) INFORMATION FOR SEQ ID NO:106:

(i) SEQUENCE CHARACTERISTICS:
        (A) LENGTH: 255 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:106:

```
Met Lys Ile Ala Pro Val Ala Ile Asn His Ser Pro Leu Ser Arg Glu
1               5                  10                  15

Val Pro Ser His Ala Ala Pro Thr Gln Ala Lys Gln Thr Asn Leu Gln
            20                  25                  30

Ser Glu Ala Gly Asp Leu Asp Ala Arg Lys Ser Ser Ala Ser Ser Pro
        35                  40                  45

Glu Thr Arg Ala Leu Leu Ala Thr Lys Thr Val Leu Gly Arg His Lys
    50                  55                  60

Ile Glu Val Pro Ala Phe Gly Gly Trp Phe Lys Lys Ser Lys
65                  70                  75                  80

His Glu Thr Gly Gly Ser Ser Ala Asn Ala Asp Ser Ser Ser Val Ala
```

-continued

```
                    85                  90                  95
Ser Asp Ser Thr Glu Lys Pro Leu Phe Arg Leu Thr His Val Pro Tyr
            100                 105                 110

Val Ser Gln Gly Asn Glu Arg Met Gly Cys Trp Tyr Ala Cys Ala Arg
            115                 120                 125

Met Val Gly His Ser Val Glu Ala Gly Pro Arg Leu Gly Leu Pro Glu
            130                 135                 140

Leu Tyr Glu Gly Arg Glu Ala Pro Ala Gly Leu Gln Asp Phe Ser Asp
145                 150                 155                 160

Val Glu Arg Phe Ile His Asn Glu Gly Leu Thr Arg Val Asp Leu Pro
                165                 170                 175

Asp Asn Glu Arg Phe Thr His Glu Glu Leu Gly Ala Leu Leu Tyr Lys
            180                 185                 190

His Gly Pro Ile Ile Phe Gly Trp Lys Thr Pro Asn Asp Ser Trp His
            195                 200                 205

Met Ser Val Leu Thr Gly Val Asp Lys Glu Thr Ser Ser Ile Thr Phe
    210                 215                 220

His Asp Pro Arg Gln Gly Pro Asp Leu Ala Met Pro Leu Asp Tyr Phe
225                 230                 235                 240

Asn Gln Arg Leu Ala Trp Gln Val Pro His Ala Met Leu Tyr Arg
                245                 250                 255
```